(12) United States Patent
Schulter

(10) Patent No.: US 6,911,046 B2
(45) Date of Patent: Jun. 28, 2005

(54) BIOCOMPATIBLE FORM AND METHOD OF FABRICATION

(75) Inventor: Carl W. Schulter, Memphis, TN (US)

(73) Assignee: Cagenix, Inc., Memphis, TN (US)

( * ) Notice: Subject to any disclaimer, the term of this patent is extended or adjusted under 35 U.S.C. 154(b) by 113 days.

(21) Appl. No.: 10/652,964

(22) Filed: Aug. 29, 2003

(65) Prior Publication Data

US 2004/0044413 A1 Mar. 4, 2004

Related U.S. Application Data

(62) Division of application No. 10/012,652, filed on Oct. 30, 2001, now Pat. No. 6,645,250.

(51) Int. Cl.[7] ................................................. A61F 2/02
(52) U.S. Cl. ................. 623/17.17; 264/222; 433/199.1; 606/151; 623/23.54
(58) Field of Search .......................... 623/17.17, 17.18, 623/23.54; 264/222, DIG. 30; 433/201.1, 199.1, 200.1; 606/151

(56) References Cited

U.S. PATENT DOCUMENTS

| | | | | |
|---|---|---|---|---|
| 3,710,789 A | * | 1/1973 | Ersek ........................... | 606/60 |
| 4,522,596 A | | 6/1985 | Ashkinazy ................... | 433/173 |
| 4,636,215 A | | 1/1987 | Schwartz ..................... | 623/16 |
| 5,380,328 A | | 1/1995 | Morgan ....................... | 606/70 |
| 5,658,516 A | | 8/1997 | Eppley et al. ............... | 264/251 |
| 5,769,637 A | | 6/1998 | Morgan ....................... | 433/176 |
| 5,839,899 A | | 11/1998 | Robinson ..................... | 433/215 |
| 6,030,218 A | | 2/2000 | Robinson ..................... | 433/173 |
| 6,152,737 A | | 11/2000 | Beaty et al. ................. | 433/172 |
| 6,217,333 B1 | | 4/2001 | Ercoli ......................... | 433/173 |
| 6,712,851 B1 | * | 3/2004 | Lemperle et al. ......... | 623/16.11 |
| 2003/0065400 A1 | * | 4/2003 | Beam et al. ............. | 623/23.51 |

FOREIGN PATENT DOCUMENTS

| | | |
|---|---|---|
| EP | 1 106 145 A2 | 6/2001 |
| FR | 2 713 090 A1 | 9/1995 |

* cited by examiner

Primary Examiner—Bruce E Snow
(74) Attorney, Agent, or Firm—Butler, Snow, O'Mara Stevens, & Cannada PLLC

(57) ABSTRACT

A biocompatible form and a method for fabricating the implant are provided. The biocompatible form may be used to support bone graft material such as that used to reconstruct missing bone in a patient's oral cavity. The implant is fabricated from a biocompatible mesh, which may be made of titanium, a titanium alloy or fiber and is permanently implantable in the patient's oral cavity. The biocompatible form has an anatomical configuration which includes one or more portions conforming substantially to various alveolar bone contours which may include predetermined, human interproximal bone contours, root prominence bone contours and mylohyoid ridge bone contours. The biocompatible form may include a palatal section. The biocompatible form may also include one or more apertures for receiving a corresponding number of dental prostheses therethrough.

14 Claims, 14 Drawing Sheets

BIOCOMPATIBLE FORM AND METHOD OF FABRICATION

CROSS-REFERENCE TO RELATED APPLICATIONS

This is a division of U.S. patent application Ser. No. 10/012,652 filed Oct. 30, 2001 now U.S. Pat. No. 6,645,250 and entitled "Biocompatible Form and Method of Fabrication". U.S. patent application Ser. No. 10/012,652 is hereby expressly incorporated by reference herein in its entirety.

STATEMENT RE FEDERALLY SPONSORED RESEARCH OR DEVELOPMENT

Not Applicable.

REFERENCE TO A "MICROFICHE APPENDIX"

Not Applicable.

BACKGROUND OF THE INVENTION

1. Field of the Invention

The present invention relates generally to bone implants and, more particularly, to biocompatible forms for use in supporting bone graft material.

2. Description of the Art

When a person experiences a loss of teeth due to trauma or other circumstances, or has teeth with periodontal disease, there is often a loss of interproximal crestal alveolar bone. This bone loss may also result in the loss of a person's interproximal or papillary oral tissue between the corresponding teeth and may cause a bone defect that is very unappealing aesthetically, and difficult to restore. The greater the atrophy of this alveolar bone, in either the maxilla or mandible, the less predictable the regeneration of this bone will be using current grafting procedures and associated structures, including those which are either permanently or temporarily implanted. Without the proper regeneration of this bone defect, any replacement tooth is likely to be mal-positioned, out of proportion and shape and form and lack interproximal tissue for a natural appearance.

The loss of teeth or periodontal disease may also result in the loss of root prominence alveolar bone, in either the maxilla or mandible. In the case of the mandible, the loss of teeth or periodontal disease may also result in a loss of mylohyoid ridge bone on either one or both sides of the mandible. Loss of root prominence alveolar bone or mylohyoid ridge bone further complicates the ability of the dentist to properly regenerate the lost bone and makes it more likely that the artificial tooth will be improperly positioned since the corresponding dental implant or support structure is supported by the root prominence bone and, depending on the particular tooth, may also be supported by the mylohyoid ridge bone.

Many attempts have been made to regenerate normal bone height and contours ranging from block grafts of bone, to grafts supported by screws or other metal supports. Known conventional graft techniques have failed to regenerate bone contours predictably and often result in placing grafted bone in locations where it is not needed, or regenerate bone that is over or under contoured. This often causes the patient to have multiple tissue and bone surgeries to correct the contours of the first graft.

One of the main goals in any attempt to replace a missing tooth is to position the tooth so that it will restore the natural appearances of the surrounding support bone and tissue. However, with the lack of bone in the atrophied maxilla or mandible, these criteria are impossible to accomplish and the results are poor with known techniques and devices. In these cases the dentist is required to restore the missing teeth and tissue contours with an artificial prosthesis, which replaces bone and soft tissue and tooth structure and may be supported by implants. The tissue and the tooth position are corrected by the prosthesis and not by the bone graft. No existing grafting technique attempts to restore the important interproximal scalloped bone contours that are critical to the proper placement of dental implants and aesthetics. One of the main problems associated with conventional methods for replacing teeth with implants is the creation of a "black hole" defect between teeth. This results from the lack of bone and tissue between the restored teeth and is very unnatural and is not aesthetically appealing to the patient.

Additional problems exist with known techniques associated with dental implants and bone grafts. For instance, dental implants are often placed in available bone or grafted bone that may not be in the proper position where teeth should be placed. The proper placement may actually be outside the dimensions of the bone. In these cases, if implants are placed in this bone, the dentist is forced to use advanced prosthetic techniques, such as angled abutments, longer transcutaneous abutments and/or custom cast abutments and frameworks to place a crown on an implant in an unnatural position. Usually, the defect is so great that the only prosthesis that can be used is the implant-supported denture, which artificially restores bone, tissue and tooth structure for the patient.

In view of the foregoing deficiencies associated with known devices and methods for regenerating dental bone in order to replace missing teeth, there remains a need for a biocompatible form and associated method for use in supporting bone graft material so that missing alveolar bone is restored to its natural contours thereby permitting dental implants to be placed in the exact position where the missing teeth were originally positioned in the skeletal bone, and allowing missing teeth to be replaced in their natural position.

BRIEF SUMMARY OF THE INVENTION

In view of the foregoing needs, the present invention is directed to a biocompatible form, which may be permanently implanted in a patient's oral cavity for use in supporting bone graft material, and a method of fabricating the biocompatible form. The biocompatible form may be advantageously utilized in either intraosseous or subperiosteal applications and the configuration of the various embodiments of the biocompatible form permit the regeneration of the scalloped alveolar bone to normal skeletal contours, for either the maxilla or mandible, thereby permitting the restoration of missing teeth in their correct position. More particularly, the biocompatible form of the present invention permits the regeneration of normal interproximal bone and tissue for an aesthetic appearance, thereby avoiding the "black hole" problems associated with conventional bone grafting techniques. Additionally, the biocompatible form permits the regeneration of root prominence root bone contours and mylohyoid ridge bone contours which contribute to the proper placement of the replacement teeth. The various configurations of the biocompatible form of the present invention permit a dentist to accurately place the bone graft material and add structural support during healing to reproduce the alveolar bone contours required to place the replacement teeth and the associated implants in the correct position.

According to a first aspect of the present invention, a biocompatible form is provided which may be permanently implanted in a patient's oral cavity for use in supporting bone graft material. The biocompatible form of the present invention is configured such that one or more portions conform to various alveolar bone contours. For instance, at least a portion of the biocompatible form may be configured to conform substantially to a predetermined, human interproximal bone contour, a root prominence bone contour, a palatal contour, a mylohyoid ridge bone contour, a maxillary facial contour, a maxillary lingual contour, a mandibular facial contour or a mandibular lingual contour.

According to a preferred embodiment, the biocompatible form is made of a first side portion, a second side portion and a connecting portion extending between and interconnecting the first and second side portions. The biocompatible form is open opposite the connecting portion and further includes open ends.

The first and second side portions and the connecting portion combine to define an interior channel, with the interior channel being sized and configured to receive at least a portion of an edentulous ridge of the patient and at least a portion of the bone graft material therewithin. The connecting portion of the biocompatible form includes at least one protruding portion, with each of the protruding portions being configured to conform substantially to a predetermined, human interproximal bone contour. The first side portion, second side portion and connecting portion are made of a biocompatible mesh. In one embodiment, the biocompatible form is a metal mesh, which may be fabricated from titanium or a titanium alloy and, in another embodiment, the biocompatible form is a fiber mesh, which may be fabricated from collagen.

In another embodiment, the biocompatible form can be configured to receive at least one dental prosthesis therethrough, with the biocompatible form further made of at least one aperture formed in the connecting portion of the biocompatible form and with each aperture sized to receive one of the dental prostheses therethrough. Each aperture is positioned intermediate an adjacent pair of the protruding portions.

In another embodiment, the first side portion of the biocompatible form may include at least one outwardly protruding portion, with each of these portions being configured to conform substantially to a predetermined human root prominence bone contour. In this embodiment, the second side portion may include at least one outwardly protruding portion, with each of the outwardly protruding portions being configured to conform substantially to a human root prominence bone contour, and with each of the outwardly protruding portions of the second side portion being aligned with one of the outwardly protruding portions of the first side portion.

In those embodiments where the first and second side portions of the biocompatible form include at least one outwardly protruding portion conforming substantially to predetermined human root prominence bone contours, each of the apertures is aligned with an aligned pair of the protruding portions of the first and second side portions, which permits each dental prosthesis to be implanted in an area of regenerated root prominence bone.

In yet another embodiment, having an application for regenerating the alveolar bone of a patient's mandible, the channel is sized and configure to receive a portion of a predetermined mandibular edentulous ridge. The second side portion may include at least one outwardly protruding each outwardly protruding of these portions being configured to conform substantially to a predetermined, human mylohyoid ridge bone contour.

In yet another embodiment, where the edentulous ridge of the patient is a maxillary ridge, the biocompatible form may further include a palatal portion integral with and extending away from the second side portion. The palatal portion being configured to conform substantially to a predetermined, human palatal bone contour.

The biocompatible mesh includes a first surface facing toward the interior channel of the biocompatible form and a second surface facing away from the interior channel. In those embodiments where the metal mesh is fabricated from either titanium or a titanium alloy, the first surface of the mesh may be sand-blasted and subsequently acid-etched to enhance adherence of the bone graph material to the biocompatible form. This applies to bone implants having either intraosseous or subperiosteal applications. Additionally, in intraosseous applications, the second surface of the mesh screen may also be sand-blasted and subsequently acid-etched to enhance the adherence of the bone graft material to the bone implant. With regard to subperiosteal applications, the second surface of the mesh may be polished to enhance adherence of the patient's oral mucosal tissue to the biocompatible form. Additionally, in these embodiments, the second surface of the mesh may be treated with titanium nitrate after the surface is polished for aesthetic purposes.

According to a second aspect of the present invention, a method is provided for fabricating a bone implant which may be permanently implanted in a patient's oral cavity for use in supporting bone graft material. According to one preferred embodiment, the method comprises the steps of acquiring a biocompatible mesh, creating a solid cast mold of an edentulous mandibular or maxillary ridge of a human cadaver skull which includes normal alveolar bone contours, and forming the biocompatible mesh to substantially conform to the contours of the solid cast mold including the contours of the mold corresponding to the normal alveolar bone contours of the human cadaver skull.

The step of forming may involve the step of press fitting the biocompatible mesh to the solid cast mold. The step of acquiring may include the step of selecting the biocompatible mesh from one of titanium, a titanium alloy and a fiber material.

The method of the present invention may be used to fabricate a biocompatible form having application as either an intraosseous implant or a subperiosteal implant. With either application, when the biocompatible mesh is made of either titanium or a titanium alloy, the method of the present invention may further include the steps of sandblasting a first surface of the biocompatible mesh which faces an interior channel defined by the mesh, and subsequently acid-etching the first surface of the mesh after the step of sandblasting, to enhance the adherence of the bone graft material to the biocompatible form. For biocompatible forms having intraosseous application, the method of the present invention may further include the steps of sandblasting a second surface of the biocompatible mesh which faces away from the interior channel, and acid-etching the second surface of the mesh after the step of sandblasting, also for the purpose of enhancing the adherence of the bone graft material to the biocompatible form.

In the instances where the biocompatible form is to be used for subperiosteal applications, the method of the present invention may further include the step of polishing the second surface of the biocompatible mesh to enhance adherence of the patient's oral mucosal tissue to the implant. In this embodiment, the method of the present invention may further include the step of treating the second surface of the biocompatible mesh with titanium nitrate, for aesthetic purposes.

According to another aspect of the invention, the biocompatible form can be customized to further conform to at least a portion of the alveolar bone contours of the patient's edentulous ridge. This method includes the steps of taking a CAT Scan of at least one of a patient's maxillary or mandibular ridge, which comprises an edentulous ridge, and fabricating a resin mold of the patient's edentulous ridge from an output of the CAT Scan.

The method of the present invention may also further involve the steps of taking an impression of a dental arch of the patient which is disposed in opposing relationship with the edentulous ridge of the patient and making a dental stone mold of the patient's dental arch. In this embodiment, the method further involves the steps of mounting the resin mold of the patient's edentulous ridge and the dental stone mold of the patient's opposing dental arch on a dental articulator, with the resin mold including an area corresponding to one or more missing teeth, and occluding a coronal portion of at least one tooth to the dental mold in a position opposite the area of missing teeth on the resin mold.

The method may further include the steps of positioning the formed biocompatible mesh on the resin mold over the area corresponding to one or more missing teeth and closing the dental articulator such that the dental stone mold is disposed in close proximity to the resin mold and the mesh screen.

According to another aspect of this invention, an intraosseous dental implant which is permanently implanted in a patient's oral cavity is provided. This dental implant is made of a membrane barrier layer, a bone graft material and a biocompatible form. This implant involves the membrane barrier layer substantially covering the bone graft material, the membrane barrier layer contacting a patient's oral mucosal tissue; the bone graft material substantially covering a biocompatible form, the biocompatible form having a first side portion, a second side portion and a connecting portion extending between and interconnecting the first and second side portions, the biocompatible form being open opposite the connecting portion and further including open ends, the first and second side portions and the connecting portion combining to define an interior channel, the interior channel being sized and configured to receive at least a portion of an edentulous ridge of the patient and at least a portion of the bone graft material therewithin; and the connecting portion including at least one protruding portion being configured to conform substantially to a predetermined, human interproximal bone contour; and at least a portion of the bone graft material disposed therewith the biocompatible form.

According to another aspect of this invention, a subperiosteal dental implant which is permanently implanted in a patient's oral cavity is provided. This dental implant is made of a membrane barrier layer, bone graft material and a biocompatible form. This implant involves the membrane barrier layer substantially covering the biocompatible form, the membrane barrier layer contacting a patient's oral mucosal tissue; the biocompatible form comprising a first side portion, a second side portion and a connecting portion extending between and interconnecting the first and second side portions, the biocompatible form being open opposite the connecting portion and further including open ends, the first and second side portions and the connecting portion combining to define an interior channel, the interior channel being sized and configured to receive at least a portion of an edentulous ridge of the patient and at least a portion of the bone graft material therewithin, the connecting portion including at least one protruding portion being configured to conform substantially to a predetermined, human interproximal bone contour, and at least a portion of the bone graft material disposed therewith the biocompatible form.

According to another aspect of this invention, an intraosseous dental implant which is permanently implanted in a patient's oral cavity is provided. This dental implant is made of a membrane barrier layer, bone graft material and a biocompatible form. This implant involves the membrane barrier layer substantially covering the bone graft material, the membrane barrier layer contacting a patient's oral mucosal tissue; the bone graft material substantially covering a biocompatible form comprising a first side portion, a second side portion and a connecting portion extending between and interconnecting the first and second side portions, the biocompatible form being open opposite the connecting portion and further including open ends, the first and second side portions and the connecting portion combining to define an interior channel, the channel being sized and configured to receive at least a portion of an edentulous ridge of the patient and at least a portion of the bone graft material therewithin; the first side portion including at least one outwardly protruding portion, each the outwardly protruding portion being configured to conform substantially to a predetermined, human root prominence bone contour; the second side portion includes at least one outwardly protruding portion, each the outwardly protruding portion being configured to conform substantially to a predetermined, human root prominence bone contour; and the first side portion, the second side portion and the connecting portion being made of a biocompatible mesh; and at least a portion of bone graft material disposed therewith the biocompatible form.

According to another aspect of this invention, a subperiostial dental implant which is permanently implanted in a patient's oral cavity is provided. This dental implant is made of a membrane barrier layer, bone graft material and a biocompatible form. This implant involves the membrane barrier layer substantially covering a biocompatible form, the membrane barrier layer contacting a patient's oral mucosal tissue, the biocompatible form comprising a first side portion, a second side portion and a connecting portion extending between and interconnecting the first and second side portions, the biocompatible form being open opposite the connecting portion and further including open ends, the first and second side portions and the connecting portion combining to define an interior channel, the channel being sized and configured to receive at least a portion of an edentulous ridge of the patient and at least a portion of the bone graft material therewithin; the first side portion including at least one outwardly protruding portion, each the outwardly protruding portion being configured to conform substantially to a predetermined, human root prominence bone contour; the second side portion includes at least one outwardly protruding portion, each the outwardly protruding portion being configured to conform substantially to a predetermined, human root prominence bone contour; and the first side portion, the second side portion and the connecting portion being made of a biocompatible mesh; and at least a portion of bone graft material being disposed therewithin the biocompatible form.

Another aspect of this invention provides a surgical kit including a sterilizable container adapted to contain articles.

This kit can include a biocompatible form which may be permanently implanted in a patient's oral cavity for use in supporting bone graft material; the biocompatible form includes a first side portion, a second side portion and a connecting portion extending between and interconnecting the first and second side portions, the biocompatible form being open opposite the connecting portion and further including open ends, the first and second side portions and the connecting portion combining to define an interior channel, the interior channel being sized and configured to receive at least a portion of an edentulous ridge of the patient and at least a portion of the bone graft material therewithin; the connecting portion including at least one protruding portion, each of the protruding portion being configured to conform substantially to a predetermined, human interproximal bone contour or portions thereof. The kit further includes a plurality of devices adapted to attach the biocompatible form to a patient's edentulous ridge and dental tools, such as a pair of molding pliers and a pair of scissors.

BRIEF DESCRIPTION OF THE DRAWINGS

These and other features, aspects and advantages of the present invention will become better understood with regard to the following description, appended claims and accompanying drawings, wherein:

DETAILED DESCRIPTION OF THE INVENTION

Figure 1:
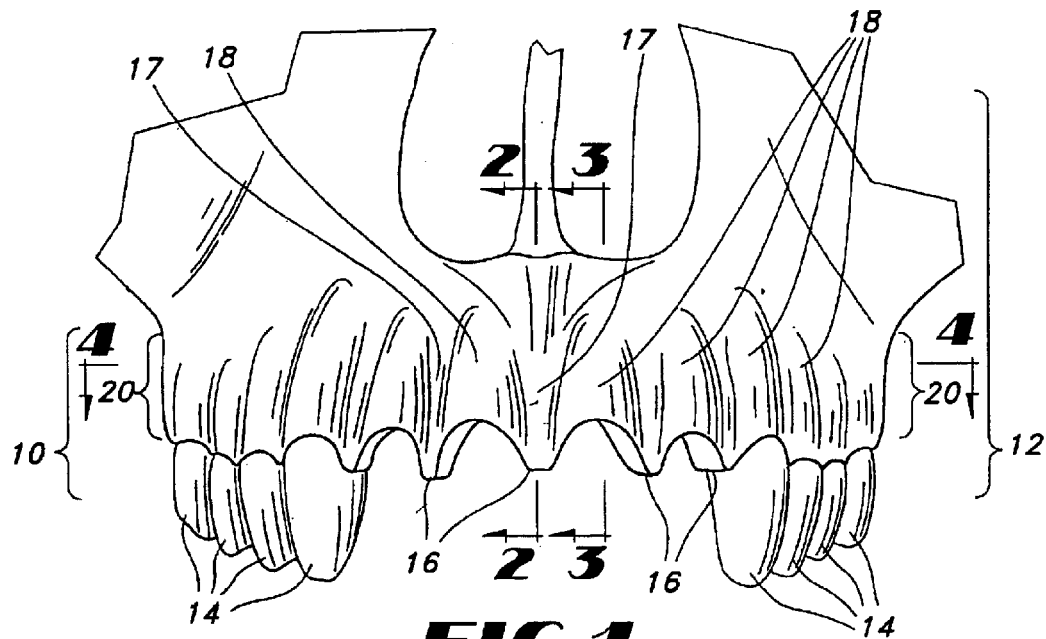
FIG. 1 is a front elevation view of upper "maxillary" arch of human skull with several teeth missing.
Figure 2:
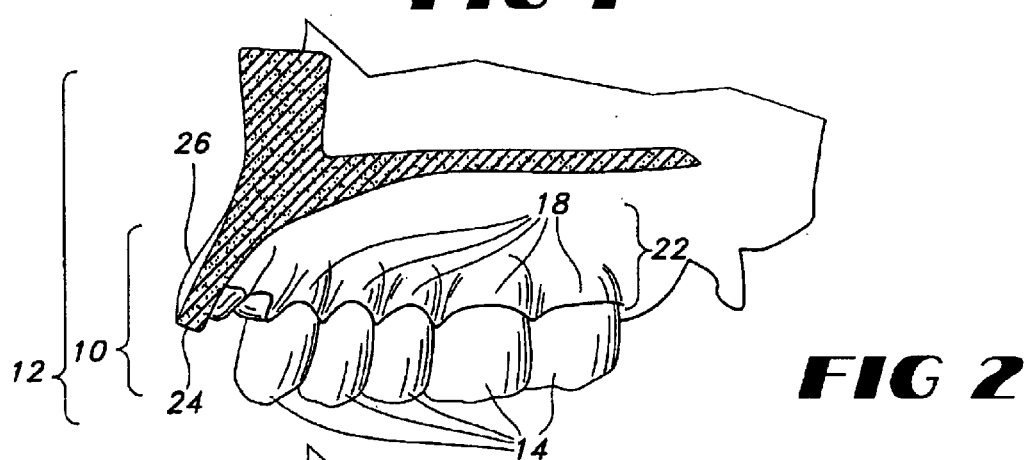
FIG. 2 is a cross-sectional view taken along line 2—2 in FIG. 1.
Figure 3:
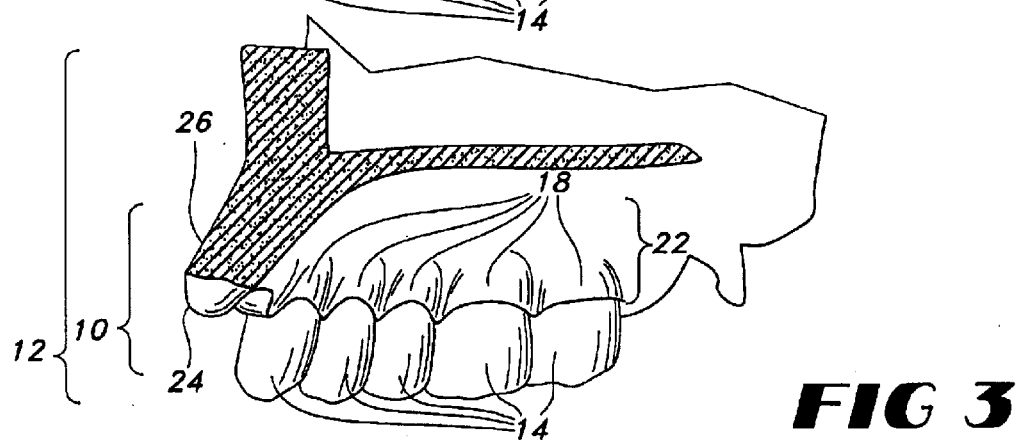
FIG. 3 is a cross-sectional view taken along line 3—3 in FIG. 1.

Referring now to the drawings, wherein like reference numerals have been used for similar elements throughout, FIGS. 1–3 are views of an upper i.e., maxillary arch 10 of a human skull 12 which includes a plurality of teeth 14. As shown in FIG. 1, the maxillary arch 10 is missing several teeth in the front, or anterior quadrant. The maxillary arch 10 further includes a plurality of circumferentially spaced interproximal bone contours 16 which are very important in positioning the teeth 14 in a vertical and horizontal direction. The plurality of interproximal bone contours 16 shown in FIG. 1 in the anterior quadrant where the teeth are missing, are illustrated as representing human interproximal bone contours. A contour is a curving or an irregular feature such as the shape of the surface. For example, as shown in FIGS. 2 and 3, bones such as the interproximal bone 24 and the root prominence bone 26 form alveolar bone contours, such as an interproximal bone contour 16 and a root prominence bone contour 18.

As may be further appreciated by reference to FIG. 1, the maxillary arch 10 includes a plurality of circumferentially spaced areas known as root prominence bone contours 18. The root prominence bone contours 18 are formed by root prominence bones 26. The plurality of root prominence bone contours 18 shown in FIG. 1 are illustrated as representing human root prominence bone contours. A maxillary facial bone contour 20 includes a plurality of root prominence bone contours 18, a plurality of the interstitial spaces 17 between root prominence bone contours 18, and a plurality of interproximal bone contours 16 on the facial side of the jaw. Maxillary facial bone contour 20 is seen on a patient's face.

FIG. 2 is a cross-sectional view through the mid-line interproximal bone 24. In FIG. 2 the maxillary lingual bone contour 22 is shown. A maxillary lingual bone contour 22 includes a plurality of root prominence bone contours 18, the interstitial space 17 between root prominence bone contours 18, and a plurality of interproximal bone contours 16 on the lingual side of the jaw. FIG. 3 is a cross-sectional view through the root prominence bone 26. The maxillary lingual bone contours 22 is also shown in this view.

Figure 4:
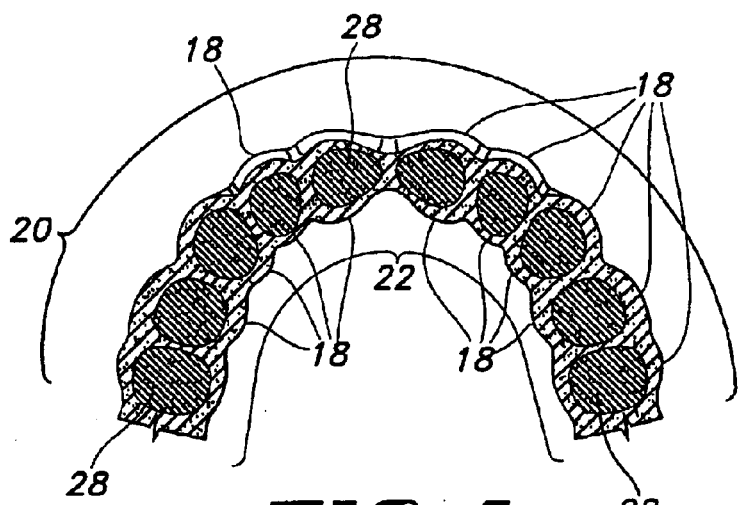
FIG. 4 is cross-sectional view taken along line 4—4 in FIG. 1.

Now referring to FIG. 4, a horizontal cross section through the maxillary arch 10 is shown. The bone 28 covering the root of the tooth 14 is the bone-forming root prominence bone contour 18. The plurality of root prominence bone contours 18 shown in FIG. 1 are illustrated as representing normal human root prominence bone contours 18. This figure also shows the maxillary lingual bone contour 22 and the maxillary facial bone contour 20. It should be noted that the size and shape of the root prominence bone contour 18 varies depending on the size and shape of the root prominence bone 26.

Figure 5:
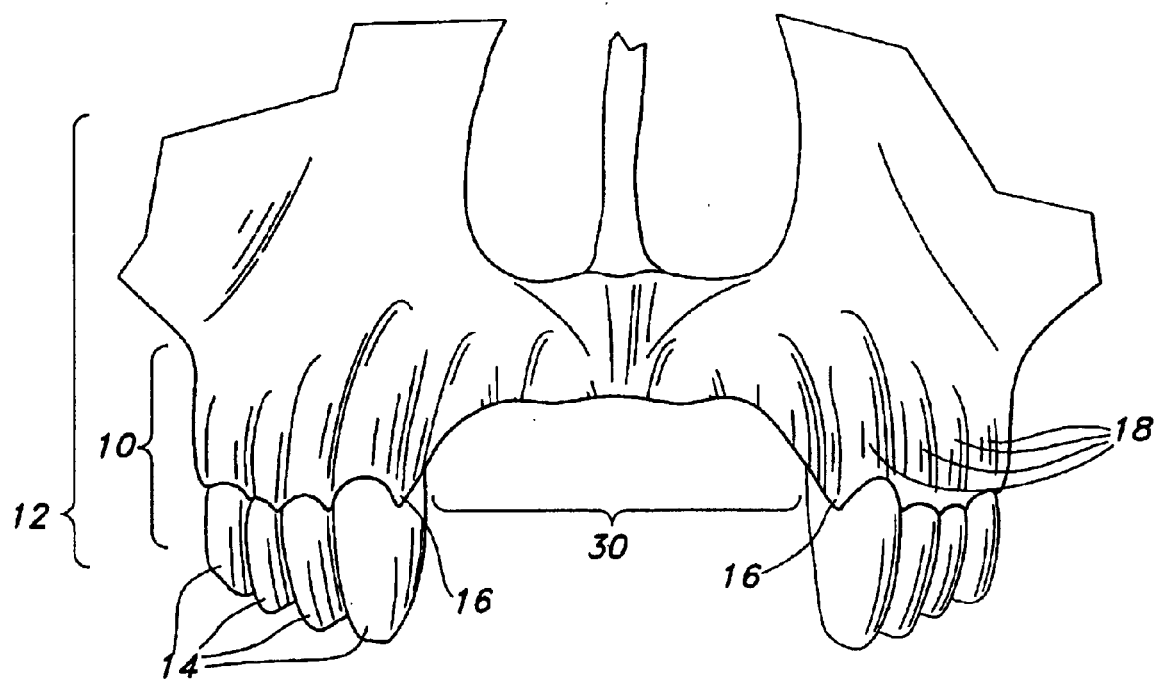
FIG. 5 is a front elevation view similar to FIG. 1, but with bone loss shown due to missing teeth.

Now referring to FIG. 5, a front elevational view of an upper i.e. maxillary arch 10 of a human skull 12 is shown, in this view, the interproximal bone contour 16 and the root prominence bone contour 18 have been removed to simulate the loss of bone in this area as the result of trauma or atrophy. This area is known as the edentulous ridge 30.

Figure 6:
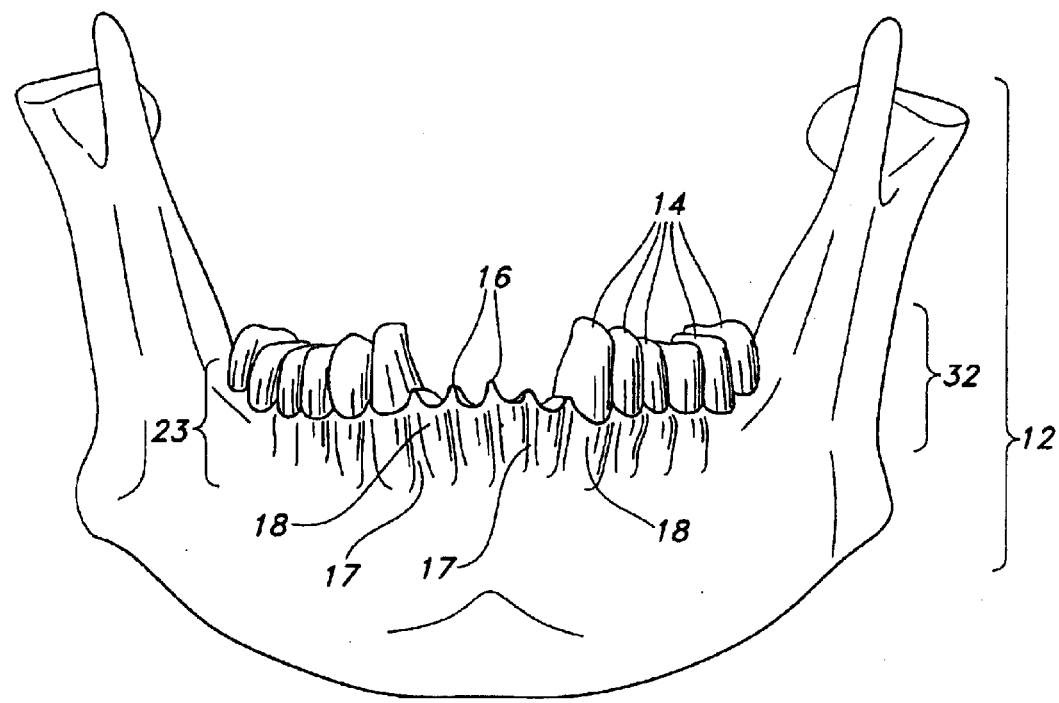
FIG. 6 is a front elevation view of bottom "mandibular" arch of human skull with several teeth missing.

FIG. 6 is a front elevation view of a lower, i.e. a mandibular arch 32 of a human skull 12, which includes a plurality of teeth 14. As shown in FIG. 6, the mandibular arch 32 is missing several teeth in the front, or anterior quadrant. The mandibular arch 32 includes a plurality of circumferentially spaced interproximal bone contours 16 which are very important in positioning teeth in a vertical and horizontal direction. The particular interproximal bone contours 16 in the anterior quadrant where the teeth are missing are illustrated as representing human interproximal bone contours 16. The mandibular arch 32 includes a plurality of circumferentially spaced areas known as root prominence bone contours 18. A mandibular facial bone contour 23 includes a plurality of root prominence bone contours 18 a plurality of interstitial spaces 17 between root prominence bone contours 18, and a plurality of interproximal bone contours 16 on the facial side of the jaw.

Figure 7:
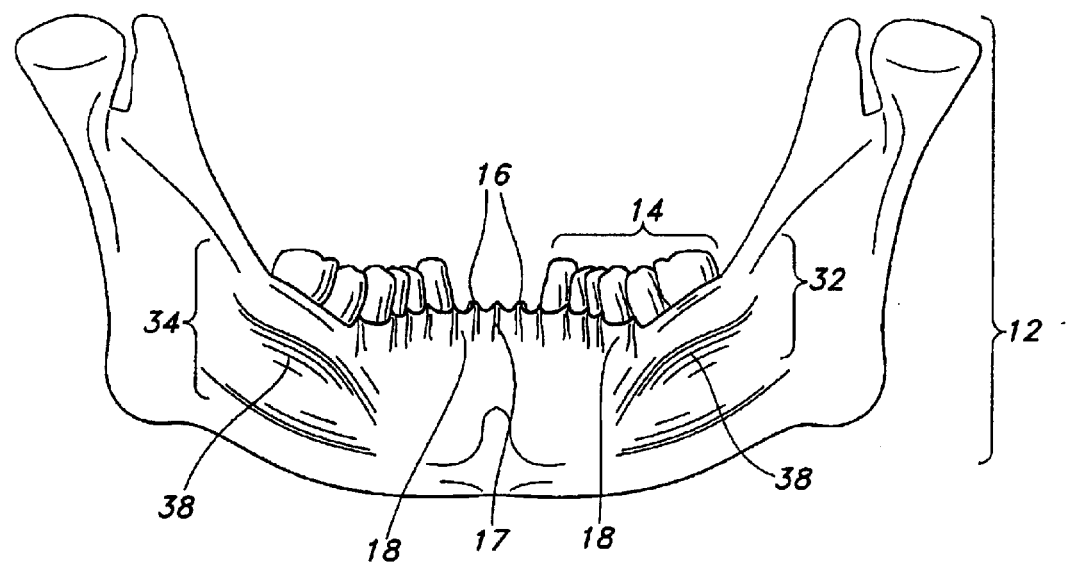
FIG. 7 is a rear elevation view of the arch shown in FIG. 6, for the purpose of illustrating the mylohyoid ridge which appears on either side of the arch.

On the lingual side of the jaw as shown in FIG. 7, a plurality of mylohyoid ridge bone contours 38 are shown in FIG. 7. The plurality of mylohyoid ridge bone contours 38 shown in FIG. 7 illustrate normal human mylohyoid ridge bone contours 38. Now referring to FIG. 7, a lingual view of FIG. 6 is shown, including the mandibular lingual bone contour 34. A lingual bone contour 34 includes a plurality of root prominence bone contours 18, a plurality of interstitial spaces 17, a plurality of interproximal bone contours 16 and a mylohyoid ridge bone contour 38 on the lingual side of the jaw.

Figure 8:
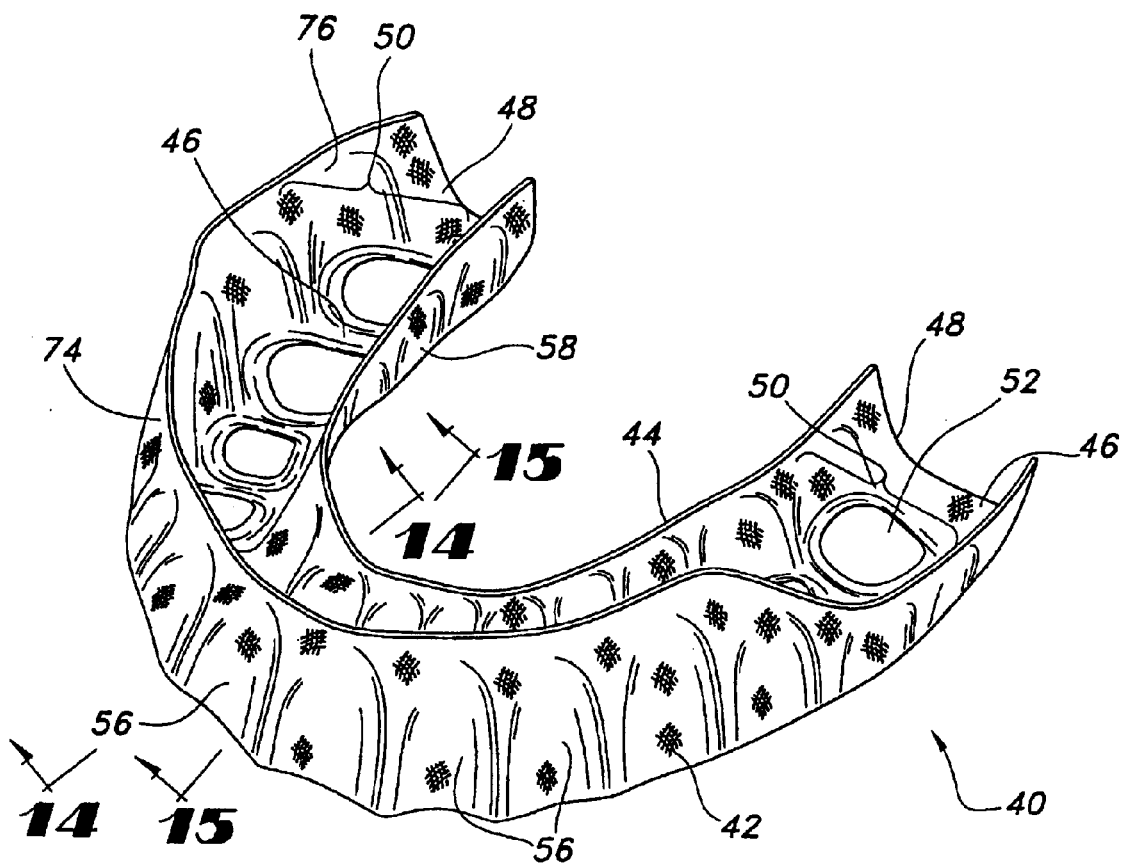
FIG. 8 is a perspective view of first embodiment of the biocompatible form of the present invention corresponding to a full upper "maxillary" dental arch.
Figure 9:
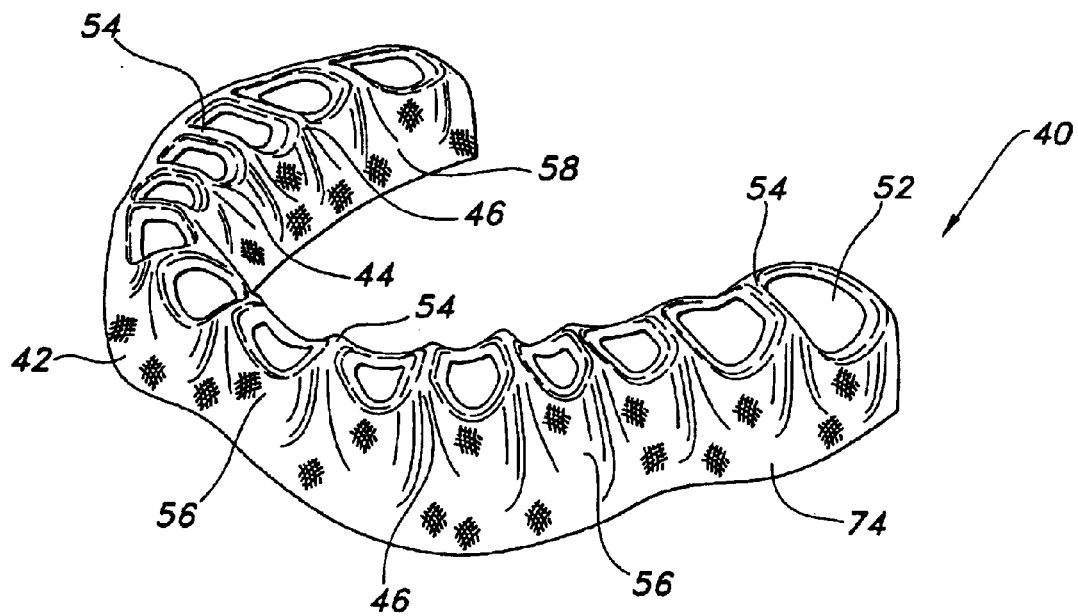
FIG. 9 is another perspective view of first embodiment of the biocompatible form of the present invention corresponding to a full upper "maxillary" dental arch.

FIGS. 8 and 9 are perspective views of one of the biocompatible forms of the present invention. The biocompatible form 40 is implanted into a patient to from a bone implant. This bone implant restores various alveolar bone contours and facilitates the implantation of a dental prosthesis. The biocompatible form 40 is filled with bone graft material to provide a bone implant. The bone graft material is placed inside of the biocompatible form 40 and then secured to an edentulous ridge 30 of the patient which corresponds to a full arch. A plurality of apertures 52 in the biocompatible form 40 are present to allow the placement of a dental prosthesis therethrough that would restore the actual tooth. More specifically, the biocompatible form 40 is made of a first side portion 42 (on the facial side), a second side portion 44 (on the lingual side), and a connecting portion 46 extending between and interconnecting the first 42 and second 44 side portions. The biocompatible form 40 is open opposite the connecting portion and further includes open ends 48. The first side portion 42, which corresponds to the facial side, the second side portion 44 which corresponds to the lingual side, and the connecting portion 46 define an interior channel 50. The interior channel 50 is sized to receive a portion of the patient's edentulous ridge 30 and at least a portion of a bone graft material.

The biocompatible form 40 is configured such that one or more portions conform to various alveolar bone contours. For example, at least a portion of the biocompatible form may be configured to conform substantially to a predetermined human interproximal bone contour 16, a root prominence bone contour 18, a mylohyoid ridge bone contour 38, a maxillary facial bone contour 20, a mandibular facial bone contour 23, a maxillary lingual bone contour 22 and a mandibular lingual bone contour 34.

More specifically, each biocompatible form described in this invention includes at least one protruding portion 54, each of the protruding portion 54 being configured to conform substantially to a predetermined human interproximal bone contour 16. When multiple protruding portions 54 exist, each of the apertures 52 are positioned circumferentially intermediate an adjacent pair of the protruding portions 54. The plurality of protruding portions 54 are circumferentially spaced from one another as shown in FIG. 9.

The biocompatible form 40 further includes at least one aperture 52 formed in the connecting portion 46 of the biocompatible form 40 and with each aperture 52 sized to receive one of the dental prostheses therethrough. The aperture can have a variety of shapes, as they are sized to receive a dental prosthesis. When multiple protruding portions 54 exist, each of the apertures 52 is positioned circumferentially intermediate an adjacent pair of the protruding portions. The protruding portions being configured to conform substantially to a predetermined human interproximal bone contour 16.

The biocompatible form 40 includes an outer surface 74 that faces away from channel 50 and an inner surface 76 that faces toward channel 50. Depending on the application of the biocompatible form 40, i.e. for use in an intraosseous implant or a subperiosteal implant, the outer surface 74 and inner surface 76 are treated differently. This method to make the biocompatible form 40 will be discussed in more detail in a later section.

Still referring to FIG. 9, this figure shows outwardly protruding portions 56 in the first side 42, the facial side. Each of the outwardly protruding portions 56 conform substantially to a predetermined, human root prominence bone contour 18. The term "predetermined" means that the contour of the biocompatible form is shaped to conform to a representative human skull from an adult male, adult female or a child. Now referring to FIG. 10, top plan view of a biocompatible form 40 is shown. This figure shows outwardly protruding portions 58 in the second side portion 44, the lingual side. Each of the outwardly protruding portions 58 conforms substantially to a predetermined human root prominence bone contour 18. Each of the outwardly protruding portions 58 of the second side portion 44 being aligned with one of the outwardly protruding portions 56 of the first side portion 42. This alignment facilitates the proper alignment of the dental prosthesis.

Figure 10:
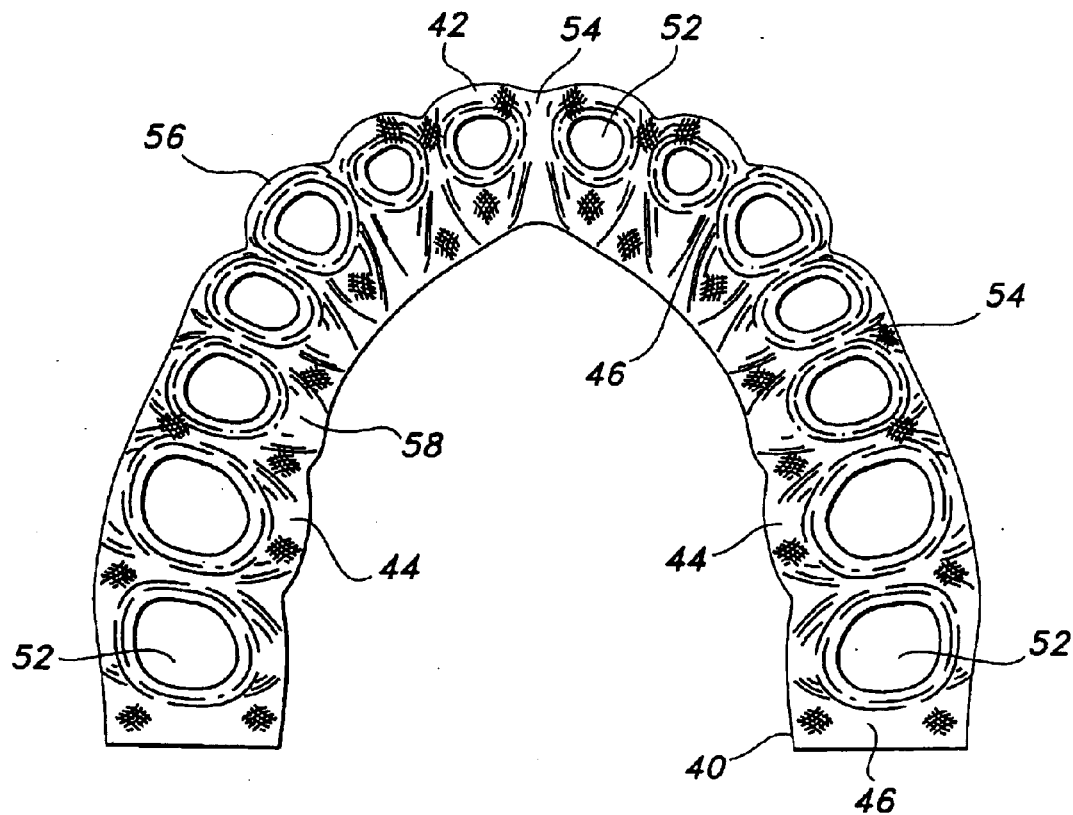
FIG. 10 is a top plan view of first embodiment of biocompatible form shown in FIG. 8.

FIG. 10 also shows apertures 52 formed in the connecting portion 46. Each aperture 52 being sized to receive one of the dental prosthesis therethrough. Each aperture 52 being aligned with one of the outwardly protruding portions 56 of the first side portion 42 and aligned with one of the outwardly protruding portions 58 of the second side portion 44.

Figure 11:
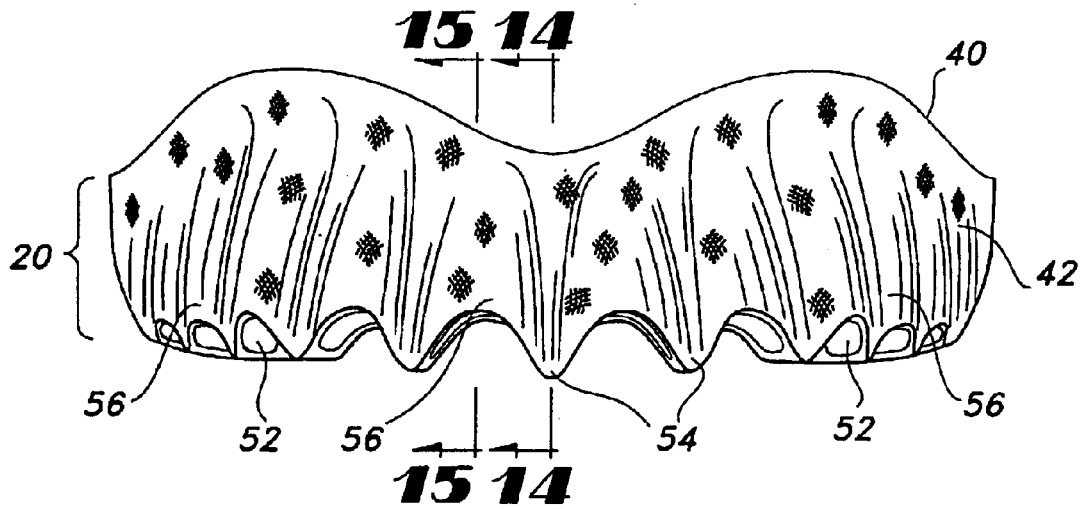
FIG. 11 is a front elevation view of first embodiment shown in FIG. 8.

Now referring to FIG. 11, a frontal view of the biocompatible form 40 is shown, including particularly the protruding portions 54 being configured to conform substantially to a predetermined, human interproximal bone contour 16. FIG. 11 also shows the first side portion 42 including a plurality of outwardly protruding portions 56, each of the outwardly protruding portions being configured to conform substantially to a predetermined human root prominence bone 18 contour (shown in FIG. 2). FIG. 11 also shows aperture 52, sized to receive one of the dental prothesis therethrough.

Figure 12:
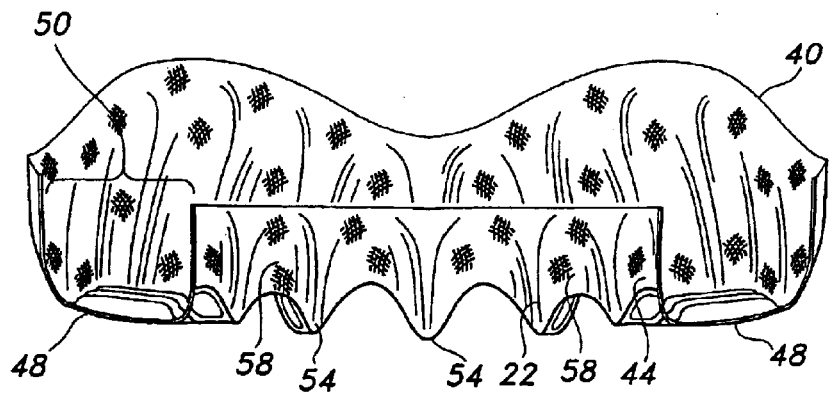
FIG. 12 is a rear elevation view of first embodiment shown in FIG. 8.

FIG. 12 is a rear view of the biocompatible form 40. This view shows the outwardly protruding portions 58 that conform substantially to a lingual contour 22 of a predetermined human root prominence bone 18 contour (shown in FIG. 1).

Figure 13:
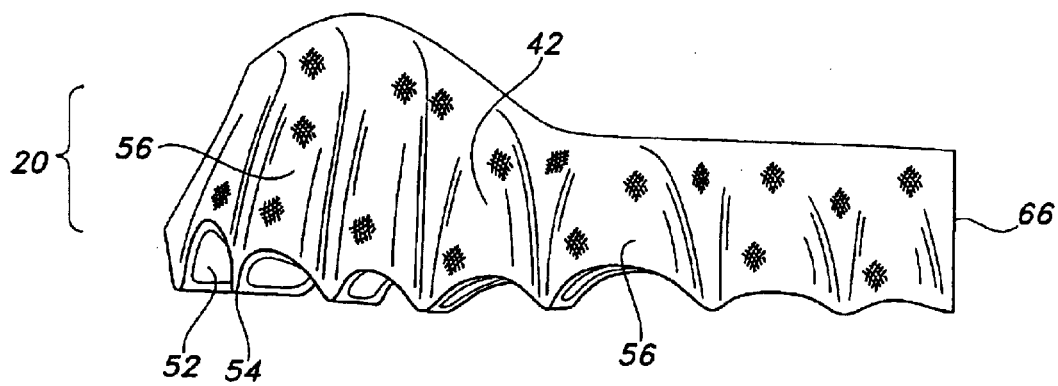
FIG. 13 is a left side elevation of view of first embodiment shown in FIG. 8.
Figure 14:
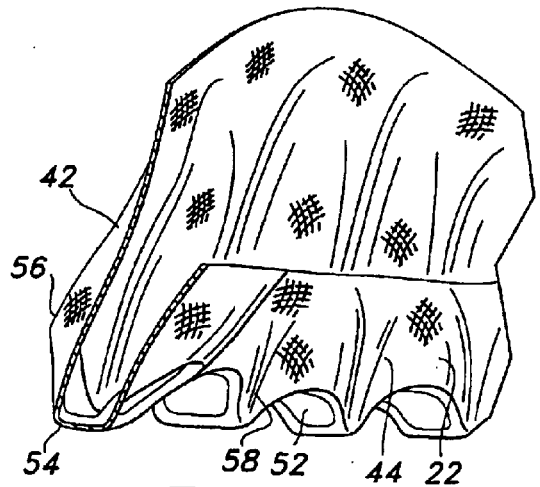
FIG. 14 is a cross-sectional view taken along line 14—14 in FIG. 11.
Figure 15:
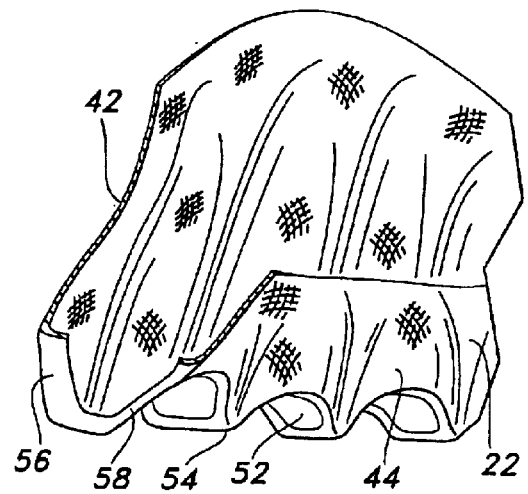
FIG. 15 is a cross-sectional view taken along line 15—15 in FIG. 11.

FIG. 13 is a left-sided, or left quadrant view of a biocompatible form. FIG. 14 is a cross-sectional view of an anterior section going through the interproximal section of the biocompatible form 40 of FIG. 8 at 14—14. FIG. 15 is a similar view going through the root prominence portion of FIG. 8 at 15—15.

Figure 16:
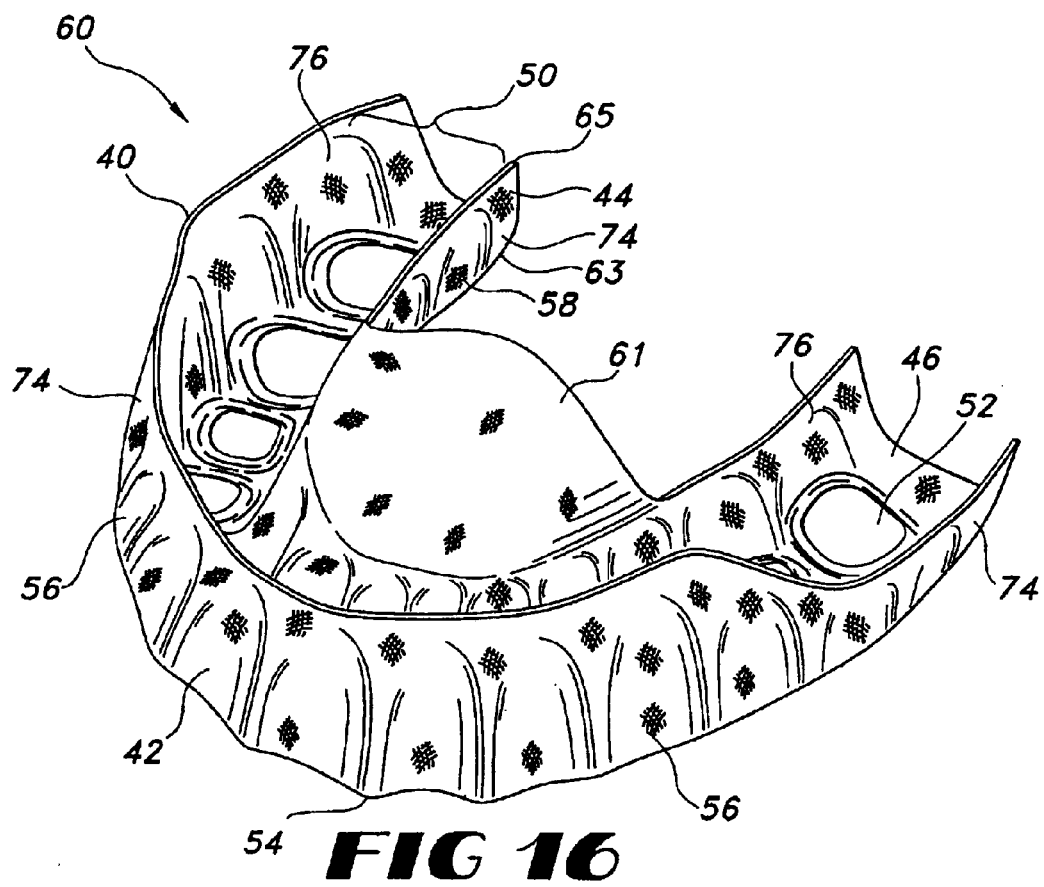
FIG. 16 is a perspective view of second embodiment of biocompatible form of present invention, which includes a portion corresponding to the palate in the upper mouth.
Figure 17:
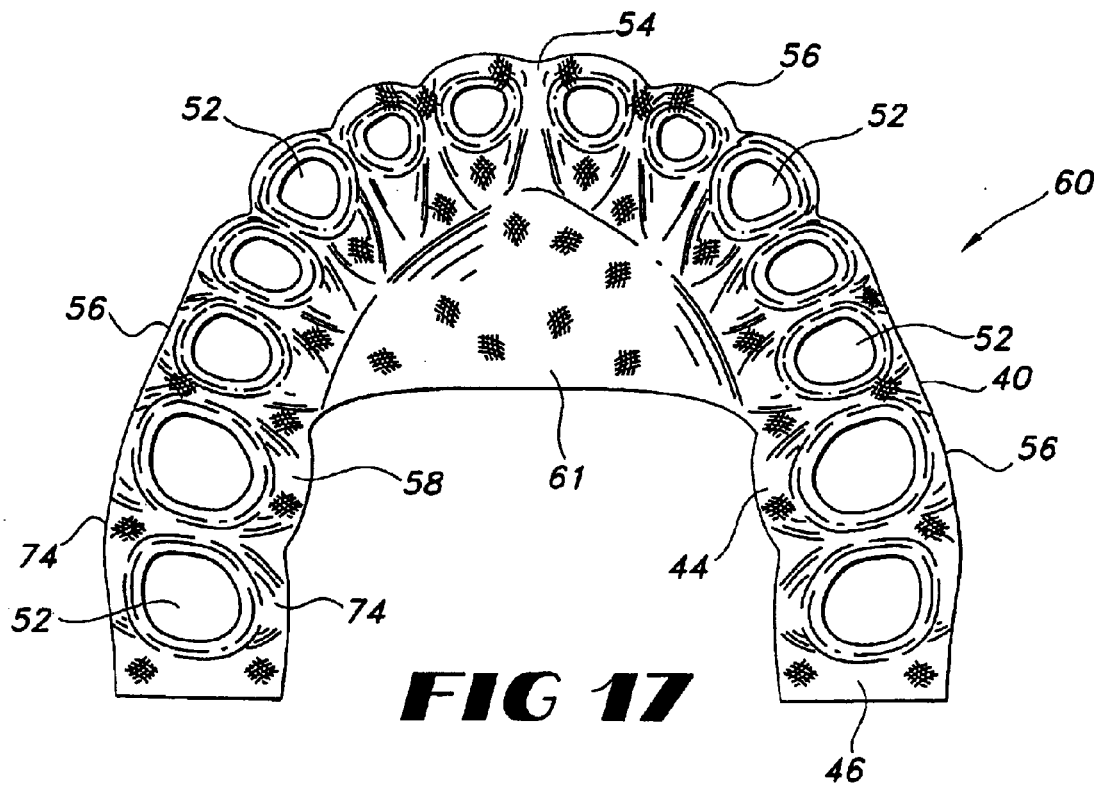
FIG. 17 is a top plan view of embodiment shown in FIG. 16.
Figure 18:
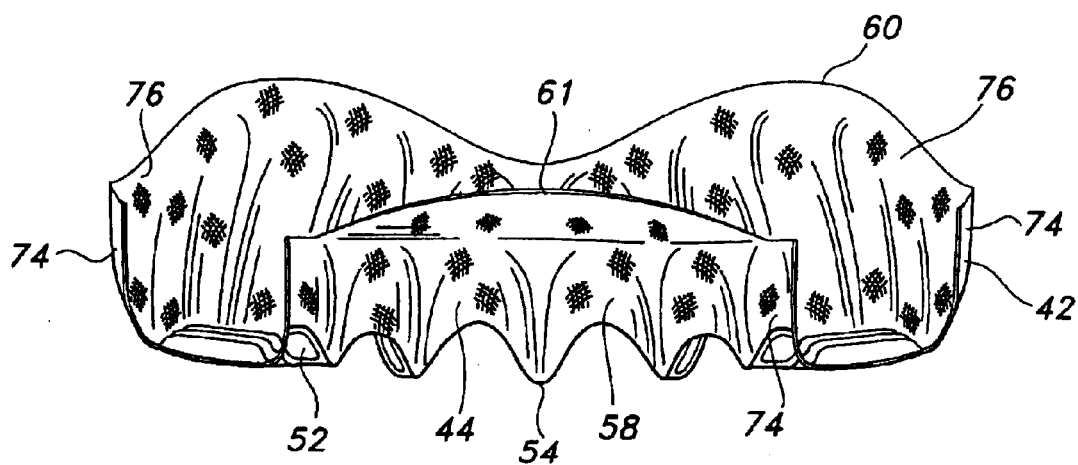
FIG. 18 is a rear view further illustrating palatal area of the embodiment shown in FIGS. 16 and 17.

In the embodiment, shown in FIGS. 16–18, a palatal section 61 of mesh is added to biocompatible form 40, as described previously, to form a biocompatible form 60 useful in the reconstruction of palatal defects. More specifically, the biocompatible form 60 may further include a palatal portion 61 integral with and extending away from the second side portion 44, i.e. the lingual side. The palatal portion 61 has an arcuate shape conforming substantially to a predetermined human palatal bone contour. In this embodiment, the second side portion 44 includes a proximal portion 63 integral with the connecting portion and a distal portion 65 opposite the proximal portion. The palatal portion 61 of the biocompatible form 60 is integral with the distal portion 65 of the second side portion 44.

The biocompatible form 60 is configured such that one or more portions conform to various alveolar bone contours. For example, at least a portion of the biocompatible form may be configured to conform substantially to a predetermined human interproximal bone contour 16, a root prominence bone contour 18, a maxillary facial bone contour 20, or a maxillary lingual bone contour 22.

Figure 22:
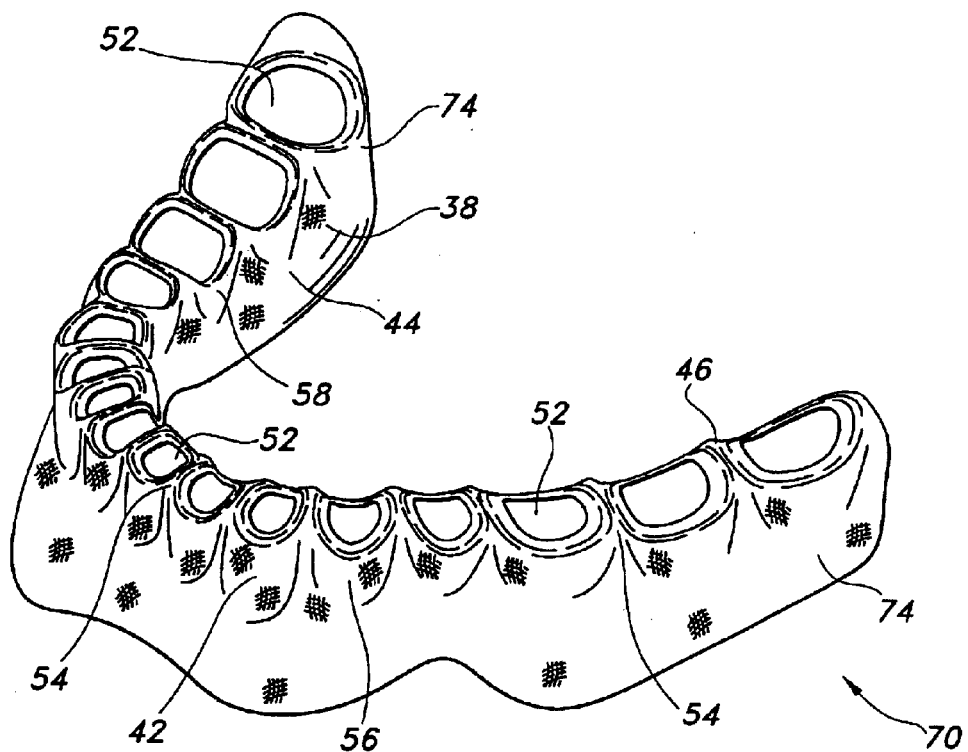
FIG. 22 is a perspective view of sixth embodiment of biocompatible form of present invention corresponding to a full lower dental arch.
Figure 23:
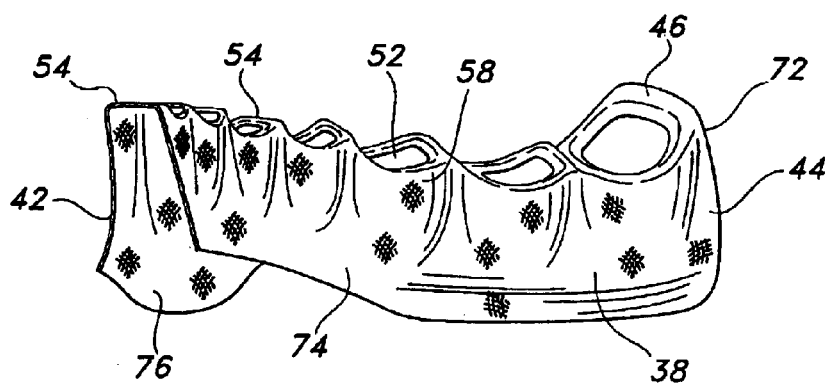
FIG. 23 is a fragmentary view of the embodiment shown in FIG. 22, to further illustrate the mylohyoid ridge bone contour.

In yet another embodiment as shown in FIGS. 22 and 23, having an application for regenerating the alveolar bone of a patient's mandible, the second side portion 44 may include at least one outwardly protruding and circumferentially extending portion 38 with each of these portions being configured to conform substantially to a predetermined, human mylohyoid ridge bone contour 38. The biocompatible form 70, shown in FIGS. 22 and 23, is configured such that one or more portions conform to various alveolar bone contours. For example, at least a portion of the biocompatible form 70 may be configured to conform substantially to a predetermined human interproximal bone contour 16, a root prominence bone contour 18 and a mylohyoid ridge bone contour 38, a maxillary facial bone contour 20, a mandibular facial bone contour 23, a mandibular lingual bone tour 34 and a maxillary bone contour 22.

Figure 19:
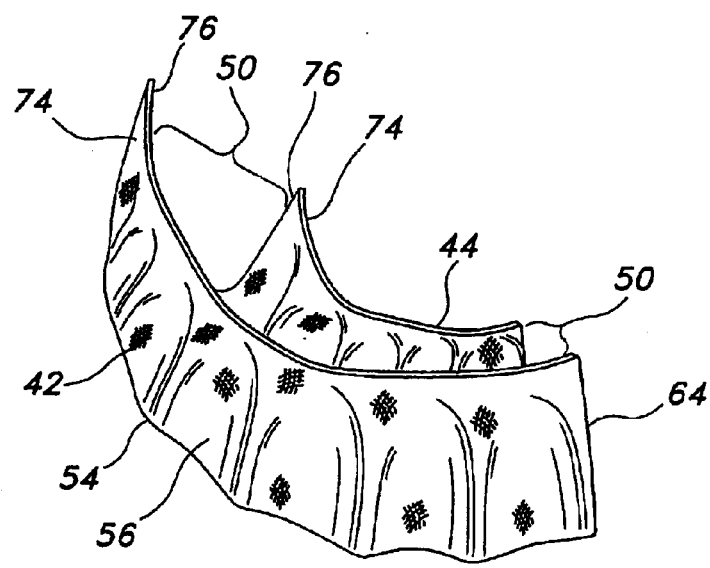
FIG. 19 is a perspective view of the third embodiment of present invention corresponding to upper, anterior quadrant portion of the biocompatible form.
Figure 20:
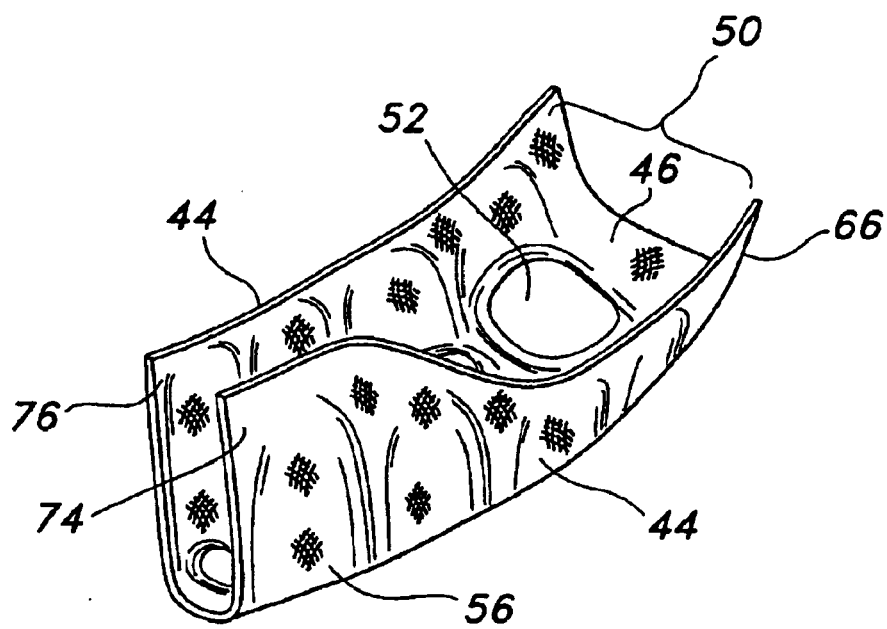
FIG. 20 is a perspective view of fourth embodiment of biocompatible form of present invention corresponding to a customized left posterior quadrant of upper dental arch.
Figure 21:
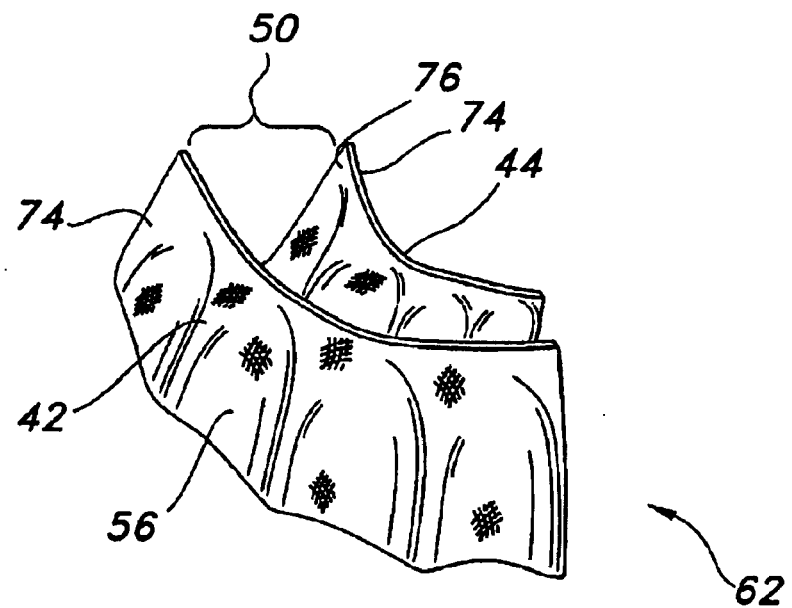
FIG. 21 is a perspective view of fifth embodiment of biocompatible form of present invention corresponding to an anterior quadrant of the upper dental arch.

In another embodiment of the invention, portions of the biocompatible form 40 and 70 are provided. In FIG. 19, for example, an anterior quadrant section of biocompatible form 64 is shown. More specifically, an anterior implant going from the right cuspid to the left cuspid area in a maxilla is shown. The quadrant section of the biocompatible form 64 includes on the first side portion 42 outwardly protruding portion 56, on the second side portion 44, outwardly protruding portion 58 (not shown) and protruding portion 54. The outer surface 74 and inner surface 76 of the quadrant section of the biocompatible form 64 are also shown. FIG. 20 is the side view on a left quadrant section 66 of a biocompatible form 40. FIG. 21 is a customized anterior implant 62 going from the right lateral incisor to the left lateral incisor, including both centrals.

Figure 24:
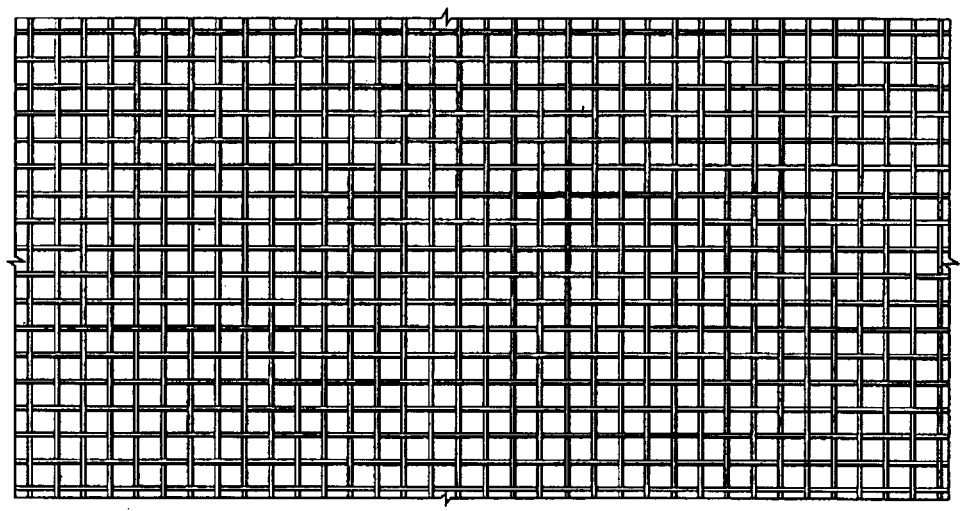
FIG. 24 is a plan view of titanium mesh sheet.

The biocompatible forms 40, 60 and 70 are made of biocompatible metal mesh such as titanium and/or titanium alloy or stainless steel, or a fibrous mesh, such as a collagen mesh. An example of a sheet of mesh is shown in FIG. 24. The mesh may also be formed from metal perforated with holes. The biocompatible form 40, 60 and 70 are pre-formed to the normal contours of the alveolar bone by press fitting the mesh to a titanium replica model of a normal edentulous ridge with alveolar bone contours. The titanium replica model is formed from an adult male, an adult female, or older child's skull. The biocompatible forms 40, 60 and 70 are configured to conform substantially to predetermined, human interproximal bone contours.

The biocompatible forms 40, 60 and 70 include a first facial side 42 and a second side lingual 44 connected by a connecting portion 46. Each side has an outer surface 74 and an inner surface 76. The outer surface 74 faces the facial or lingual side of the form and the inner surface 76 faces the interior channel 50. In those embodiments where the biocompatible forms 40, 60 and 70 are made of a metal wire mesh screen fabricated from either titanium or a titanium alloy, the inner 76 surfaces of the mesh screen may be sandblasted and subsequently acid-etched to enhance adherence of the bone graft material to the biocompatible form 40, 60 and 70. This applies to biocompatible forms 40 having either intraosseous or subperiosteal applications. Additionally, in intraosseous applications, the outer 74 surfaces of the biocompatible form 40, 60 and 70 may also be sandblasted and subsequently acid-etched, according to conventional procedures, to enhance the adherence of the bone graft material to the biocompatible form 40 and 70. With regard to subperiosteal applications, the outer 74 surfaces of the biocompatible form 40 may be satin polished with a polishing wheel to enhance adherence of the patient's oral mucosal tissue to the dental implant. Additionally, in these embodiments, the outer 74 surfaces of the biocompatible form 40 may be treated with titanium nitrate after the surface is polished for aesthetic purposes to prevent a metal, such as titanium from showing through the tissue.

According to a second aspect of the present invention, a method is provided for fabricating biocompatible forms 40, 60 and 70, which may be permanently implanted in a patient's oral cavity for use in supporting bone graft material. According to one preferred embodiment, the method involves the steps of acquiring a biocompatible screen, creating a solid cast mold of an edentulous mandibular or maxillary ridge of a human cadaver skull which includes normal alveolar bone contours, and forming the biocompatible screen to substantially conform to the contours of the solid cast mold including the contours of the mold corresponding to the normal alveolar bone contours of the human cadaver skull. The step of forming may involve the step of press fitting the biocompatible screen to the solid cast mold. The step of acquiring may involve the step of selecting the biocompatible mesh from one of titanium, a titanium alloy, wire mesh and a fiber mesh.

Figure 25:
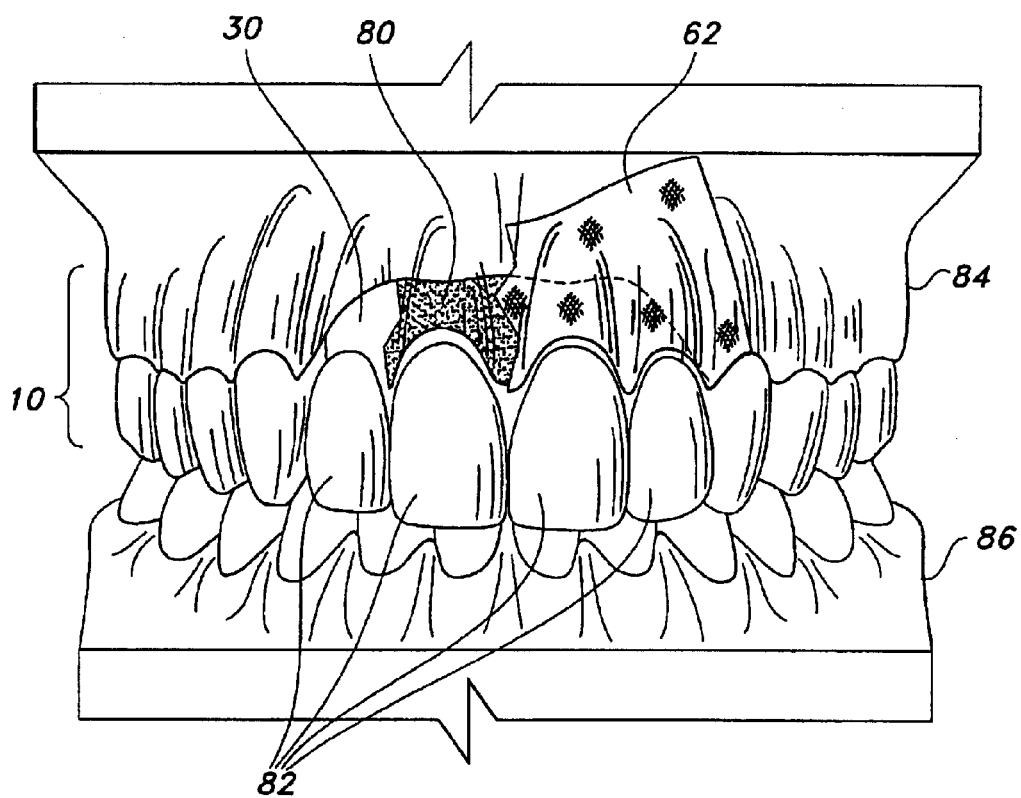
FIG. 25 is a front elevation view of a dental articulator illustrating the following features: lower arch casting with full set of teeth; resin mold of upper dental arch, created from computer model and illustrating areas of missing teeth; crown portion bonded to corresponding lower teeth; mesh implant installed on upper arch, an illustration of bone graft material and portion of the articulator.

FIG. 25 is a representation of a technique for customizing the biocompatible form 40 to conform to at least a portion of the alveolar bone contours of a particular patient's edentulous ridge. First, an endentuolus ridge 30 is shown, next to the normal maxillary arch 10, an area that represents the grafted bone material 80 is shown, and going further to the right, the biocompatible form 62 is shown. In this figure, the replacement of the missing teeth of the laterals and the centrals 82 are also shown.

More particularly, this method involves the steps of taking a CAT scan of at least one of a patient's maxillary or mandibular ridge, which includes an edentulous ridge 30, and fabricating a resin mold 84 of the patient's edentulous ridge from an output of the CAT scan. The method of the present invention may also further involve the steps of taking an impression of a dental arch 86 of the patient which is disposed in opposing relationship with the edentulous ridge 30 of the patient and making a dental stone mold of the patient's dental arch 86. In this embodiment, the method further involves the steps of mounting the resin mold 84 of the patient's edentulous ridge 30 and the dental stone mold of the patient's opposing dental arch on a dental articulator with the resin mold 84 including an area corresponding to one or more missing teeth, and occluding a coronal portion of at least one tooth 82 to the dental stone mold in a position opposite the area of missing teeth on the resin mold. A dental articulator is a device that can simulate movements of the jaw. This articulated relationship of the edentulous resin cast to the dental stone mold of the patients' opposing dental arch allows for customization of the mesh to incorporate the unique contours, for example, of the interproximal bone contour, root prominence bone contour, and additionally palatal bone contour and mylohyoid bone contour. It also allows the surgeon to estimate the amount of bone graft material needed to regenerate the lost bone.

The method may further include the steps of positioning the modified biocompatible form 40, 60 or 70 on the resin mold over the area corresponding to one or more missing teeth and closing the articulator such that the dental stone mold 86 is disposed in close proximity to the resin mold 84 and the biocompatible form 40, 60 or 70. The method may further include the step of customizing the biocompatible form 40 to further conform to at least a portion of the alveolar bone contours of the patient's edentulous ridge 30. The biocompatible form 40, 60 and 70 may be further customized using dental tools such as pliers and scissors to fit a particular patient.

The method of the present invention may be used to fabricate a biocompatible form 40, 60 or 70 having application as either an intraosseous implant or a subperiosteal implant. The method of the present invention may further include the steps of sandblasting the interior channel 50 surfaces of the biocompatible form 40, 60 or 70. This includes the inner surfaces 76 of the first side 42, the second side 44 and the connecting portion 46. These surfaces will be acid-etched to enhance the adherence of the bone graft material to the biocompatible form 40, 60 or 70. For biocompatible forms 40, 60 or 70 having an intraosseous application, the method of the present invention may further include the steps of sandblasting the outer surfaces 74 of the first side facial portion 42, the second side lingual portion 44 and the connecting portion 46. This will also be acid-etched to enhance the adherence of the bone grafting material to the biocompatible form 40, 60 and 70.

In the instances where the biocompatible forms 40, 60 and 70 is to be used for subperiosteal applications, the method of the present invention may further include the step of satin polishing the outer surfaces 74 of the biocompatible form 40 to enhance adherence of the patient's oral mucosal tissue to the implant. In this embodiment, the method of the present invention may further include the step of treating the second surface of the biocompatible forms 40, 60 and 70 with titanium nitrate, for aesthetic purposes.

Figure 26:
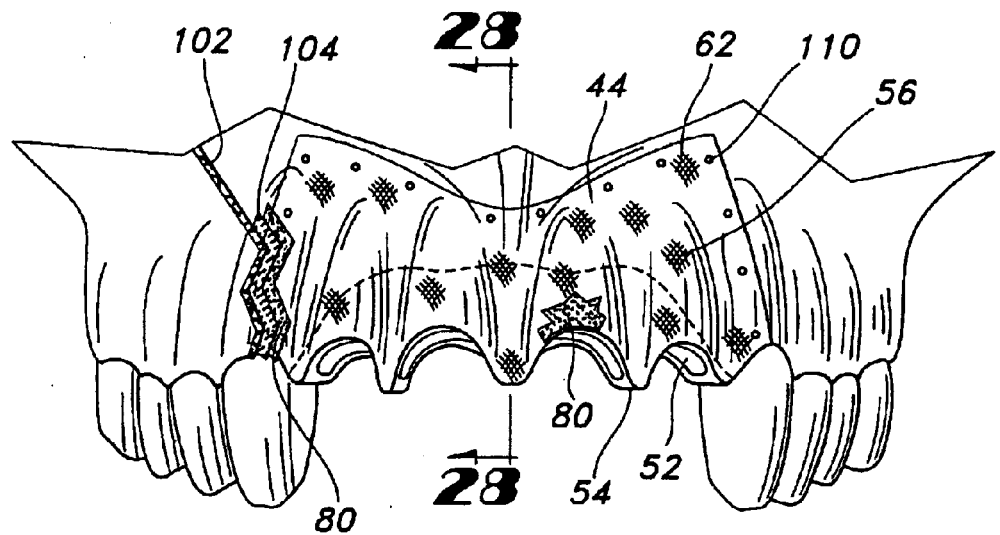
FIG. 26 is a front elevation view of a dental implant of the present invention.
Figure 27:
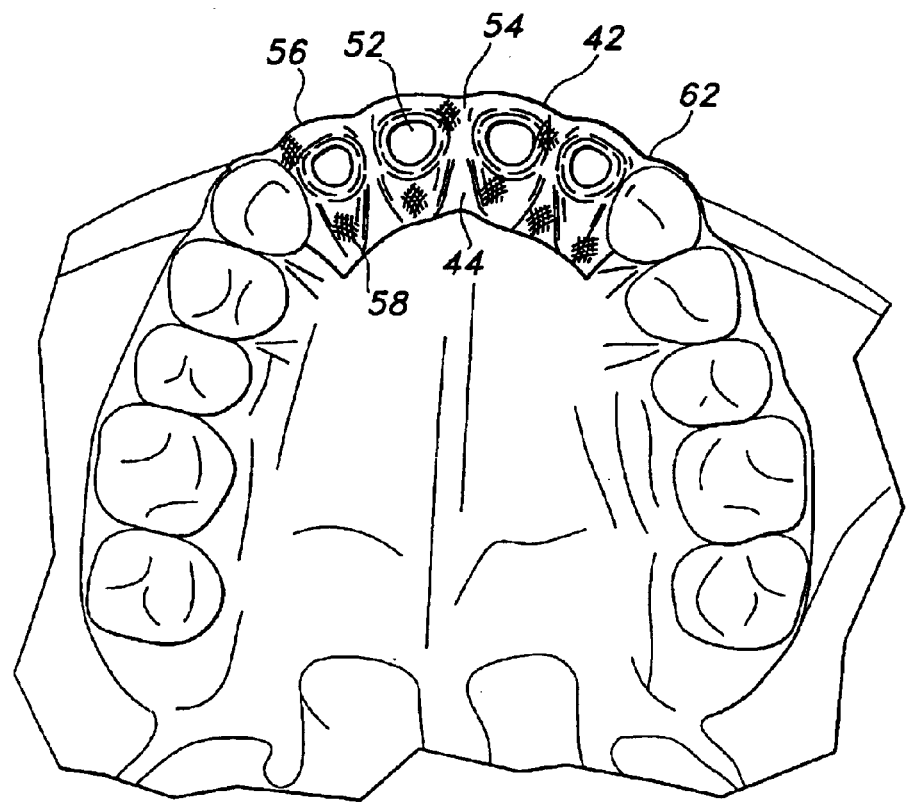
FIG. 27 is a top view of dental implant shown in FIG. 26.

FIGS. 26–27 is a graphic representation of a intraosseous bone implant 62 shown in FIG. 21. FIG. 26 shows the multiple layers for an intraosseous bone implant 62. The outer layer being the oral mucosal tissue 102. The oral mucosal tissue is retracted prior to inserting the intraosseous bone implant 62 and then re-applied to contact a membrane barrier layer 104. A membrane barrier layer 104 acts as a barrier to tissue to prevent the tissue from obstructing bone healing. This membrane barrier layer 104 is typically absorbable and is preferably collagen. A variety of membrane barrier layers are used with bone implants and it is within the skills of the surgeon to select a suitable membrane barrier layer. The membrane barrier layer 104 in an intraosseous bone implant substantially covers the bone grafted material.

Figure 28:
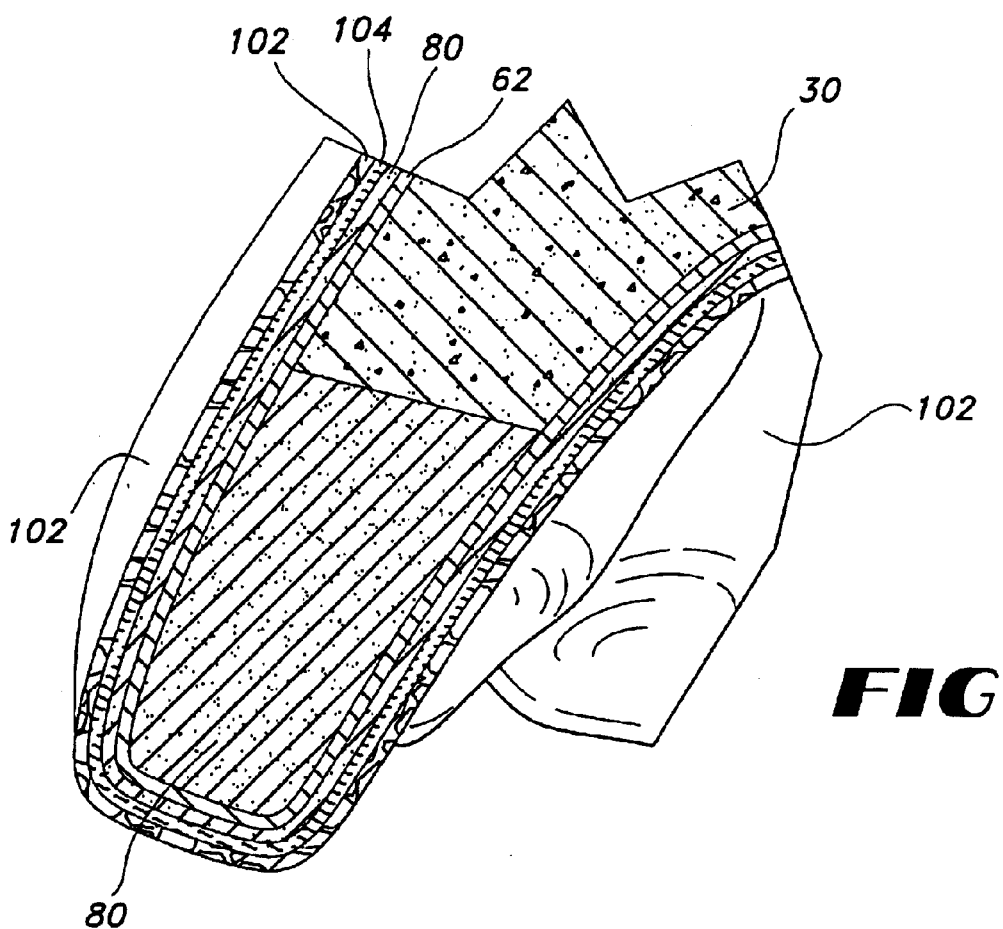
FIG. 28 is a cross-sectional view taken along line 28—28 in FIG. 26.

The next layer is the bone grafted material 80, which is overlayed onto the biocompatible form 62 and substantially covers the biocompatible form 62. The next layer is the biocompatible form 62, and then the final layer is the grafted bone material 80 within the bone implant 62. This figure also shows a plurality of the bone tacks 110 for holding the bone graft in place into the ridge. The bone tacks are titanium screws on tacks or a reabsorbable bone tack. FIG. 28 is a cross-section view of FIG. 26. It is a cross-sectional view through the interproximal bone 26 of the bone implant 62. This figure also shows the residual edentulous ridge 30 within the bone implant 62. More specifically in an intraosseous implant, a second layer of graft material 80 is applied over the bone implant 62. The bone graft material is autogenous from patient's own bone, such as the hip or from surgical site, and/or allographic material from artificial bone, such as cadavers or animal bones, mixed with plasma proteins and normal saline, as known in dental arts.

Figure 29:
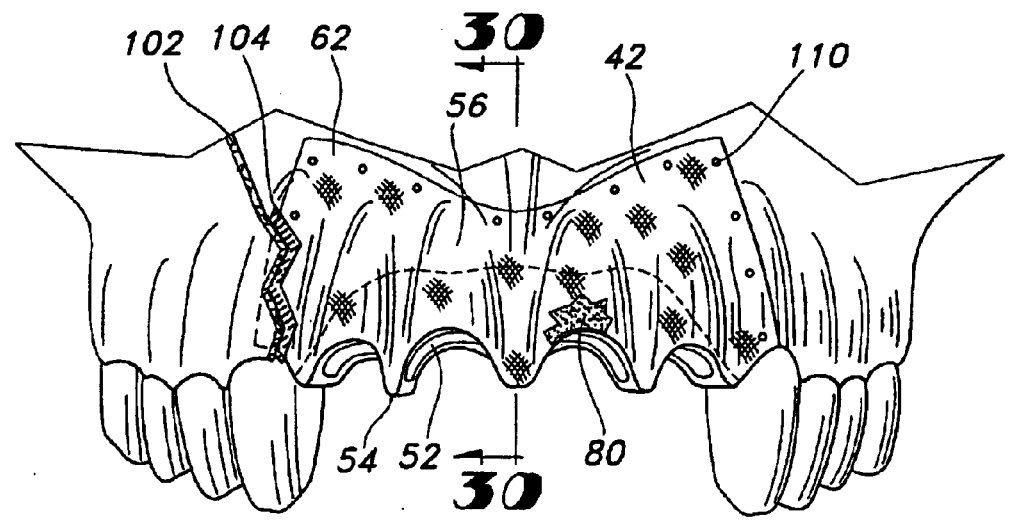
FIG. 29 is a front elevation view of another embodiment of a dental implant of the present invention.
Figure 30:
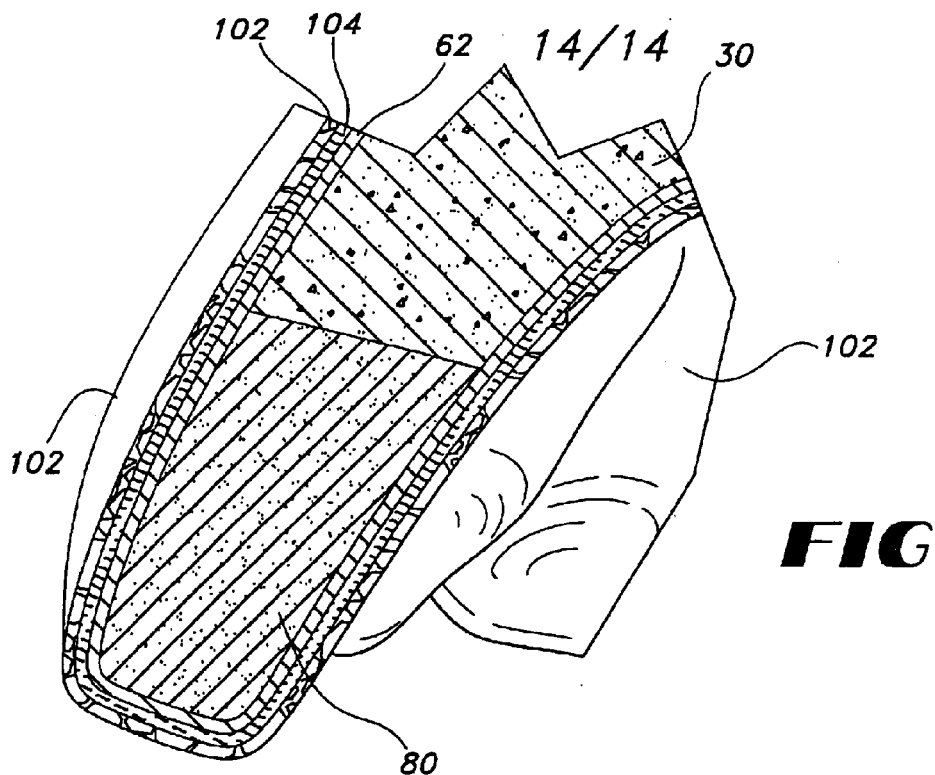
FIG. 30 is a cross-sectional view taken along line 30—30 in FIG. 29.

FIG. 29 is a subperiostial implant. The difference between the subperiostial and the intraosseous bone implant is the overlay of the bony graft material on top of the bone implant 62 and the surface preparation of the bone implant. In a subperiostial implant, as shown in FIG. 29 and cross-section view 30, a membrane barrier layer 104 substantially covers a customized biocompatible form 62. The biocompatible form 62 contacts a layer of the patient's oral mucosal tissue 102. The biocompatible form 62 is substantially filled with bone graft material 80. FIG. 30 also shows the edentulous ridge 30 within the biocompatible form 62.

Figure 31:
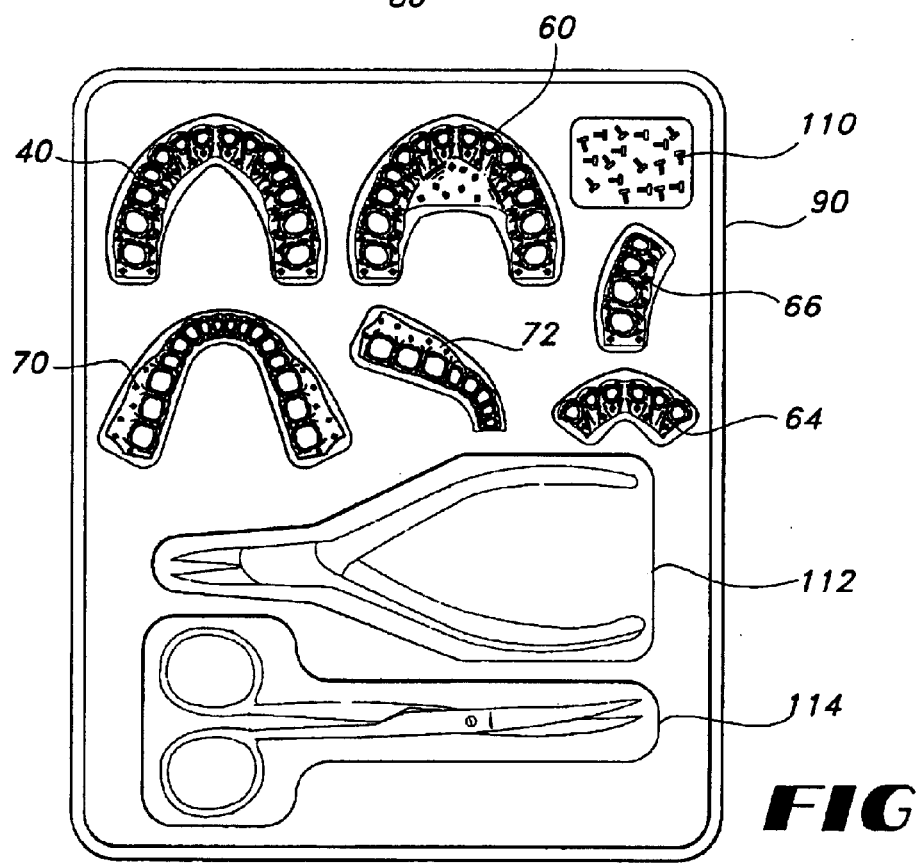
FIG. 31 is a plan view of a surgical kit made according to the present invention.

FIG. 31 is a representation of a surgical kit. The biocompatible forms included in surgical kit 90 can be for either an intraosseal or for subperiostial applications, depending on the treatment of the surface of the biocompatible form. Consequently, two types of surgical kits 90 are contemplated by this invention. More specifically, a customized biocompatible form 62 may be permanently implanted in a patient's oral cavity for use in supporting the bone graft material in a subperiosteal application. A biocompatible form for use in a subperiosteal application is made of a metal mesh. The metal mesh as formed into a biocompatible form includes a first surface facing toward the interior channel, and a second surface facing away from the interior channel. In a subperiosteal application, the second surface of the biocompatible form is polished to enhance adherence of the patient's oral mucosal tissue to the biocompatible form.

In an alternative embodiment of the kit, the kit 90 includes a biocompatible form treated for use in an intraosseous application. In a biocompatible form for use in an intraosseous application, all surfaces are sand blasted and subsequently acid etched to enhance the adherence of the bone graft material to the biocompatible form.

Each surgical kit, as shown in FIG. 31, may include biocompatible forms 40 and 70, for a complete edentulous arch of the maxilla and mandible arch respectively. It may also include portions thereof of the complete arch such as anterior 64 and posterior quadrants 66 and 72 left and right of each arch. A biocompatible form 60 for the maxilla, which includes the palatal mesh, may also be included. A pair of titanium molding pliers 112 and scissors 113 are included in the surgical kit 90. A plurality of devices, such as bone screws 110, adapted to attach the biocompatible form to the residual ridge are also included. The surgical kit 90 is made of a sterilizable container adapted to contain various biocompatible forms, a pair of titanium molding pliers 112, scissors, 113, and a plurality of bone screws. The surgical kit 90 can be sterilized using a conventional means, such as ETO.

The biocompatible form is pre-formed to normal contours of the alveolar bone by press fitting the biocompatible forms 40, 60 or 70 to a titanium replica model of a normal endentulous ridge to replicate bone contours. The biocompatible form 40, 60 or 70 can be cut into arch quadrants and surfaces prepared. The biocompatible form 40, 60 or 70 prepared for intraosseous application is totally sand blasted with small particles of titanium and acid etched. The subperiosteal implants under surface is also sand blasted and acid etched and the tissue surfaces are satin polished. The biocompatible forms 40, 60 and 70 can also be treated with titanium nitrate. They are sterilized and packaged. The biocompatible form 40 is made in various gauges and mesh sizes.

EXAMPLE 1—Intraosseous Implant

A patient with missing teeth requires restoration. A CAT scan of the area to be regenerated along with its surround arch form is performed. A computer-generated resin model of the existing bony contours and the remaining dental arch is fabricated. The model is mounted on articulator (Whipmix®, Lexington, Ky.) with the opposing arch. The missing teeth on the resin model are positioned in a normal anatomic position to determine the amount and contours of the bone to be regenerated. Wax or other medium is applied to the resin model to simulate the contours of the bone. The model is duplicated by conventional means. An intraosseous biocompatible form from the kit shown in FIG. 31 is selected that matches the patient. A biocompatible form 40 or 70 for a complete edentulous arch of the maxilla or mandible arch respectively, can be used or a biocompatible form such as 62, which is a portion of the full arch, can be used. The surgeon selects a biocompatible form that more closely matches the needed restoration. In this example, a biocompatible form 40, corresponding to a full arch is cut to precise form with titanium scissors and place on the duplicated model. The mesh can be recontoured with molding pliers to exactly fit the model and the desired regenerated contours. The biocompatible form 40 is sterilized by conventional means and prepared for surgical placement.

At the time of surgery, the tissue is reflected and graft site prepared. The biocompatible form is filled with an autogenous and/or an allographic material such as Bio-Oss® Concellus or Bio-Oss® Contical (OsteoHealth Co., Shirley, N.Y.) and secured to prepared bony receptor site with reabsorbable fixation pins. In this case, an intraosseo implant, the biocompatible form is placed 1–2 mm below the actual regenerated contours to allow for placement of graph material over the top of the biocompatible form. An absorbable collagen membrane, such as Bio-Gide® (OsteoHealth, Co., Shirley, N.Y.) is placed over the intraosseo implant and tissue closed for primary healing. The graft site is allowed to heal for six months with no pressure on the graft area. After healing is completed, dental prosthesis may be placed in the apertures.

EXAMPLE 2—Subperiosteal Implant

A patient with missing teeth requires restoration. A CAT scan of the area to be regenerated along with its surround arch form is performed. A computer-generated resin model of the existing bony contours and the remaining dental arch is fabricated. The model is mounted on articulator (Whipmix®, Lexington, Ky.) with the opposing arch. The missing teeth on the resin model are positioned in a normal anatomic position to determine the amount and contours of the bone to be regenerated. Wax or other medium is applied to the resin model to simulate the contours of the bone. The model is duplicated by conventional means. A subperiosteal biocompatible form from the kit shown in FIG. 31 is selected that matches the patient. The biocompatible form 40 is cut to precise form with titanium scissors and place on the duplicated model. The mesh can be recontoured with molding pliers to exactly fit the model and the desired regenerated contours. The biocompatible form 40 is sterilized by conventional means and prepared for surgical placement.

At the time of surgery, the tissue is reflected and grafted site prepared. The biocompatible form is filled with autogenous and/or allographic material such as Bio-Oss® Concellus or Bio-Oss® Conticol (OsteoHealth Co., Shirley, N.Y.) and secured to prepare bony receptor site with titanium screws or tacks. In a subperiosteal implant, a collagen membrane, such as Bio-Gide® (OsteoHealth Co., Shirley, N.Y.) is placed directly on the biocompatible form and the tissue closed for primary healing. The graft site should be allowed to heal for six months with no pressure on the graft area. After healing is complete, dental implants may be placed in the designed receptor sites.

EXAMPLE 3—Palatal Defect Restoration

If a patient is missing palatal bone and several teeth due to surgery from a cancerous tumor, the procedures set out in Example 1 or 2 are repeated, but with the exception of a biocompatible form 60 having palatal area 61 is selected from the surgical kit 90.

While the foregoing description has set forth the various embodiments of the present invention in particular detail, it must be understood that numerous modifications, substitutions and changes can be undertaken without departing from the true spirit and scope of the present invention as defined by the ensuing claims. The invention is therefore not limited to specific preferred embodiments as described, but is only limited as defined by the following claims.

What is claimed is:

1. A method for fabricating a biocompatible form which may be permanently implanted in a patient's oral cavity for use in supporting bone graft material, said method comprising the steps of:

acquiring a biocompatible mesh;

creating a solid cast mold of an edentulous mandibular or maxillary ridge of a human cadaver skull which includes normal alveolar bone contours;

forming the biocompatible mesh to substantially conform to the contours of the solid cast mold including the contours of the mold corresponding to the normal alveolar bone contours of the human cadaver skull.

2. The method as recited in claim 1, wherein said step of forming comprises the step of:

press fitting the biocompatible mesh to the solid cast mold.

3. The method as recited in claim 1, wherein said step of acquiring comprises the step of:

selecting the biocompatible mesh from one of titanium, a titanium alloy, and a fiber material.

4. The method as recited in claim 1, further comprising the steps of:

taking a CAT Scan of at least one of a patient's maxillary or mandibular ridge, the ridge comprising an edentulous ridge;

fabricating a resin mold of the patient's edentulous ridge from an output of the CAT Scan.

5. The method as recited in claim 4, further comprising the steps of:

taking an impression of a dental arch of the patient which is disposed in opposing relationship with the edentulous ridge of the patient;

making a dental stone mold of the patient's dental arch.

6. The method as recited in claim 5, further comprising the steps of:

mounting the resin mold of the patient's edentulous ridge and the dental stone mold of the patient's opposing dental arch on a dental articulator, the resin mold including an area corresponding to one or more missing teeth;

occluding a coronal portion of at least one tooth to the dental stone mold in a position opposite the area of missing teeth on the resin mold.

7. The method as recited in claim 6, further comprising the steps of:

positioning the formed biocompatible mesh on the resin mold over the area corresponding to one or more missing teeth;

closing the articulator such that the dental stone mold is disposed in close proximity to the resin mold and the mesh screen.

8. The method as recited in claim 7, further comprising the step of:

customizing the biocompatible form to further conform to at least a portion of the alveolar bone contours of the patient's edentulous ridge.

9. The method as recited in claim 1, wherein the biocompatible screen is made of one of titanium and a titanium alloy and is configured to define an interior channel, wherein said method further comprises the step of:

sandblasting a first surface of the biocompatible screen which faces toward the interior channel to enhance the adherence of the bone graft material to the biocompatible form.

10. The method as recited in claim 9, further comprising the step of:

acid-etching the first surface of the biocompatible mesh after said step of sandblasting to further to enhance the adherence of the bone graft material to said biocompatible form.

11. The method as recited in claim 10, further comprising the step of:

sandblasting a second surface of the biocompatible mesh which faces away from the interior channel to enhance the adherence of the bone graft material to the biocompatible form.

12. The method as recited in claim 10, further comprising the step of:

acid-etching the second surface of the biocompatible mesh after the step of sand-blasting the second surface to further enhance the adherence of the bone graft material to the biocompatible form.

13. The method as recited in claim 10, further comprising the step of:

polishing a second surface of the biocompatible screen which faces away from the interior channel to enhance adherence of the patient's oral mucosal tissue to the biocompatible form.

14. The method as recited in claim 12, further comprising the step of:

treating the second surface of the biocompatible mesh with titanium nitrate.

\* \* \* \* \*